US008140270B2

(12) United States Patent
Kingsmore et al.

(10) Patent No.: US 8,140,270 B2
(45) Date of Patent: Mar. 20, 2012

(54) METHODS AND SYSTEMS FOR MEDICAL SEQUENCING ANALYSIS

(75) Inventors: Stephen F. Kingsmore, Santa Fe, NM (US); Damian D. G. Gessler, Santa Fe, NM (US); Gregory D. May, Santa Fe, NM (US); Joann Mudge, Santa Fe, NM (US)

(73) Assignee: National Center for Genome Resources, Santa Fe, NM (US)

( * ) Notice: Subject to any disclaimer, the term of this patent is extended or adjusted under 35 U.S.C. 154(b) by 548 days.

(21) Appl. No.: 12/054,072

(22) Filed: Mar. 24, 2008

(65) Prior Publication Data

US 2009/0183268 A1     Jul. 16, 2009

Related U.S. Application Data

(60) Provisional application No. 60/919,435, filed on Mar. 22, 2007.

(51) Int. Cl.
*G06F 19/10* (2011.01)
*G06F 19/14* (2011.01)
(52) U.S. Cl. ............................ 702/19; 702/20
(58) Field of Classification Search .................. None
See application file for complete search history.

(56) References Cited

U.S. PATENT DOCUMENTS

| 2006/0228744 | A1 | 10/2006 | Hashmi et al. ........... 435/6 |
| 2007/0166707 | A1 | 7/2007 | Schadt et al. ........... 703/11 |
| 2010/0183610 | A1* | 7/2010 | Li et al. .................. 424/134.1 |
| 2011/0098193 | A1 | 4/2011 | Kingsmore et al. ...... 703/11 |

FOREIGN PATENT DOCUMENTS

WO    WO 2011/050341    4/2011

OTHER PUBLICATIONS

Altshuler et al. "An SNP Map of the Human Genome Generated by Reduced Representation Shotgun Sequencing." 2000, Nature, vol. 407, pp. 513-516.
Bainbridge et al. "Analysis of the Prostate Cancer Cell. Line LNCaP Transcriptome Using a Sequencing-by-synthesis Approach." 2006, BMC Genomics, vol. 7, pp. 246.
Balasubramanian et al. "Sequence Variation in G-protein-coupled Receptors: Analysis of Single Nucleotide Polymorphisms." 2005, Nucleic Acids Res., vol. 33(5), pp. 1710-1721.
Balderas et al. "Genetics of Schizophrenia: Preliminary Findings on 18p in the Costa Rica Population." 2001, 2001 Annual Meeting of the American College of Neuropsychopharmacology.
Barbosa et al. "Identification of Mutations in Two Major mRNA Isoforms of the Chediak-Higashi Syndrome Gene in Human and Mouse." 1997, Hum. Mol. Genet., vol. 6(7), pp. 1091-1098.
Barbosa et al. "Identification of the Homologous Beige and Chediak-Higashi Syndrome Genes." 1996, Nature, vol. 382(6588), pp. 262-265.

Bardelli et al. "Mutational Analysis of the Tyrosine Kinome in Colorectal Cancers." 2003, Science, vol. 300(5621), pp. 949.
Benjamini et al. "Controlling the False Discovery Rate in Behavior Genetics Research." 2001, Behav. Brain. Res., vol. 125(1-2), pp. 279-284.
Berrettini WH. "Are schizophrenic and bipolar disorders related? A review of family and molecular studies." 2000, Biol Psychiatry, vol. 48(6), pp. 531-538 (Abstract Only).
Botstein et al. "Discovering Genotypes Underlying Human Phenotyes Past Successes for Mendelian Disease, Future Approaches for Complex Disease." 2003, Nat. Genet., vol. 33 Suppl. 228-237.
Buetow et al. "Reliable Identification of Large Numbers of Candidate SNPs from Public EST Data." 1999, Nat. Genet., vol. 21, pp. 323-325.
Buetow, K.H. "Cyberinfrastructure: Empowering a 'Third Way' in Biomedical Research." 2005, Science, vol. 308(5723), pp. 821-824.
Camargo et al. "The Contribution of 700,000 ORF Sequence Tags to the Definition of the Human Transcriptome." 2001, PNAS, vol. 98, pp. 12103-12108.
Carter, C.J. "Schizophrenia Susceptibility Genes Converge on Interlinked Pathways Related to Glutamatergic Transmission and Long-term Potentiation, Oxidative Stress, and Oligodendrocyte Viability." 2006, Schizophr. Res., vol. 86(1-3), pp. 1-14 (Abstract Only).
Chaisson et al. "Fragment Assembly with Short Reads." 2004, Bioinformatics, vol. 20(13),pp. 2067-2074. Cheung et al. "Sequencing *Medicago truncatula* Expressed Sequence Tags Using the 454 Life Sciences Technology." 2006, BMC Genomics, vol. 7, pp. 272.
Cooper et al. "The GP Problem: Quantifying Gene-to-phenotype Relationships." 2002, In Silico Biology, vol. 2, pp. 151-164.
Cox et al. "Integrating Gene and Protein Expression Data: Pattern Analysis and Profile Mining." 2005, Methods, vol. 35(3), pp. 303-314.
Current Announcements regarding FTP repository of dbSNP data, Revised Aug. 6, 2008, available at fttp://ftp.ncbi.nih.gov/snp/00readme.txt (retrieved Jul. 20, 2009).

(Continued)

*Primary Examiner* — Lori A Clow
(74) *Attorney, Agent, or Firm* — Ballard Spahr LLP

(57) ABSTRACT

Disclosed are methods of identifying elements associated with a trait, such as a disease. The methods can comprise, for example, identifying the association of a relevant element (such as a genetic variant) with a relevant component phenotype (such as a disease symptom) of the trait, wherein the association of the relevant element with the relevant component phenotype identifies the relevant element as an element associated with the trait, wherein the relevant component phenotype is a component phenotype having a threshold value of severity, age of onset, specificity to the trait or disease, or a combination, wherein the relevant element is an element having a threshold value of importance of the element to homeostasis relevant to the trait, intensity of the perturbation of the element, duration of the effect of the element, or a combination. The disclosed methods are based on a model of how elements affect complex diseases. The disclosed model is based on the existence of significant genetic and environmental heterogeneity in complex diseases. Thus, the specific combinations of genetic and environmental elements that cause disease vary widely among the affected individuals in a cohort. The disclosed model is an effective, general experimental design and analysis approach for the identification of causal variants in common, complex diseases by medical sequencing. The disclosed model and the disclosed methods based on the model can be used to generate valuable and useful information.

37 Claims, 15 Drawing Sheets

OTHER PUBLICATIONS

Detter et al. "Rab Geranylgeranyl transferase alpha Mutation in the Gunmetal Mouse Reduces Rab Prenylation and Platelet Synthesis." 2000, PNAS, vol. 97(8), pp. 4144-4149.

Do et al. "Schizophrenia: Glutathione Deficit in Cerebrospinal Fluid and Prefrontal Cortex in vivo." 2000, Eur. J. Neurosci., vol. 12(10), pp. 3721-3728 (Abstract Only).

Dressman et al. "Transforming Single DNA Molecules into Fluorescent Magnetic Particles for Detection and Enumeration of Genetic Variations." 2003, PNAS, vol. 100(15), pp. 8817-8822.

Elston et al. "The Prior Probability of Autosomal Linkage." 1975, Ann. Hum. Genet., vol. 38, pp. 341-350.

Emrich et al. "Gene Discovery and Annotation Using LCM-454 Transcriptome Sequencing." 2007, Genome Res., vol. 17(1), pp. 69-73.

Eschenbach et al. Executive Summary—"Toward a Comprehensive Genomic Analysis of Cancer," Jul. 20-22, 2005, available at http://cancergenome.nih.gov/about/TCGA_executive_summary.pdf.

Ewing B et al. "Base-calling of automated sequencer traces using phred. II. Error probabilities." 1998, Genome Res., 8:186-94.

Ewing et al. "Base-calling of Automated Sequencer Traces Using Phred. I. Accuracy Assessment." 1998, Genome Res., vol. 8, pp. 175-185.

Freimer et al. "The Use of Pedigree, Sib-Pair and Association Studies of Common Diseases for Genetic Mapping and Epidemiology." 2004, Nat. Genet., vol. 36(1), pp. 1045-1051.

Glazier et al. "Finding Genes that Underlie Complex Traits." 2002, Science, vol. 298(5602), pp. 2345-2349.

Goldberg et al. "A Sanger/pyrosequencing Approach for the Generation of High-quality Draft Assemblies of Marine Microbial Genomes." 2006, PNAS, vol. 103(30), pp. 11240-11245.

Goldberg et al. "Executive Subprocesses in Working Memory: Relationship to Catechol-O-methyltransferase Val158Met Genotype and Schizophrenia." 2003, Arch. Gen. Psychiatry, vol. 60(9), pp. 889-896.

Gottesman II et al. "The Endophenotype Concept in Psychiatry: Etymology and Strategic Intentions." 2003, American J Psychiatry, vol. 160, pp. 636-645.

Gowda et al. "Robust Analysis of 5'-Transcript Ends (5' RATE): A Novel Technique for Transcriptome Analysis and Genome Annotation." 2006, Nucleic Acids Res., vol. 34(19), pp. e126.

Grima et al. Dopamine-induced Oxidative Stress in Neurons with Glutathione Deficit: Implication for Schizophrenia. 2003, Schizophr. Res., vol. 62(3), pp. 213-224 (Abstract Only).

Hampe et al. "A Genome-wide Association Scan of Nonsynonomous SNPs Identifies a Susceptibility Variant for Crohn Disease in ATG16L1." 2007, Nat. Genet., vol. 39(2), pp. 207-211.

Harlan et al. "The Human Myristoylated Alanine-rich C Kinase Substrate (MARCKS) gene (MACS): Analysis of its Gene Product, Promoter, and Chromosomal Localization." 1991, J. Biol. Chem., vol. 266(22), pp. 14399-14405.

Harrison et al. "Six Degrees of Separation: On the Prior Probability that Schizophrenia Susceptibility Genes Converge on Synapses, Glutamate and NDMA Receptors." 2006, Mol. Psychiatry, vol. 11(11), pp. 981-983.

Hasler et al. "Toward Constructing an Endophenotype Strategy for Bipolar Disorders." 2006, Biol. Psychiatry, vol. 60, pp. 93-105.

Helgason et al. "Refining the Impact of TCF7L2 Gene Variants on Type 2 Diabetes and Adaptive Evolution." 2007, Nat. Genet., 39(2), pp. 218-225.

Henikoff et al. "Amino Acid Substitution Matrices from Protein Blocks." 1992, PNAS, vol. 89(22), pp. 10915-10919.

Hey et al. "Cyberinfrastucture for e-Science." 2005, Science, vol. 308(5723), pp. 817-821 (Abstract only).

Horvath et al. "Family-based Tests for Associating Haplotypes with General Phenotype Data: Application to Asthma Genetics." 2004, Genet. Epidemiol., vol. 26(1), pp. 61-69.

International Human Genome Sequencing Consortium. "Finishing the Euchromatic Sequence of the Human Genome." 2004, Nature, vol. 431, pp. 931-945.

Kimchi-Safarty et al. "A 'Silent' Polymorphism in the MDR1 Gene Changes Substrate Specificity." 2007, Science, vol. 315(5811), pp. 525-528.

Kingsmore et al. "Glycine Receptor beta-Subunit Gene Mutation in Spastic Mouse Associated with LINE-1 Element Insertion." 1994, Nat. Genet., vol. 7(2), pp. 136-141 (Abstact Only).

Kingsmore, S.F. "Multiplexed Protein Measurement: Technologies and Applications of Antibody Arrays." 2006, Nat. Rev. Drug Discov., vol. 5, pp. 310-321.

Knight, J.C. "Regulatory Polymorphisms Underlying Complex Disease Traits." 2005, J. Mol. Med., vol. 83(2), pp. 97-109.

Kuhnlein et al. "The Dynamics of the Genotype-phenotype Association." 2003, Poult. Sci., vol. 82, pp. 876-881.

Lange et al. "A Multivariate Family-based Association Test Using Generalized Estimating Equations: FBAT-GEE." 2003, Biostatistics, vol. 4(2), pp. 195-206.

Li et al. "A Family-based Association Study of Kinesin Heavy Chain Member 2 Gene (KIF2) and Schizophrenia." 2006, Neurosci. Lett., vol. 407(2), pp. 151-155 (Abstract Only).

Li et al. "Hermansky-Pudlak Syndrome Type 7 (HPS-7) Results from Mutant Dysbindin, a Member of the Biogenesis of Lysosome-related Organelles Complex 1 (BLOC-1)." 2003, Nat. Genet., vol. 35(1), pp. 84-89.

Li et al. "Imbalanced Free Radicals and Antioxidant Defense Systems in Schizophrenia: A Comparative Study." 2006, J. Zhejiang Univ. Sci. B., vol. 7(12), pp. 981-986.

Li et al. "Genetical Genomics: Combining Genomics with Gene Expression Analysis." 2005, Hum. Mol. Genet., vol. 14 Spec No. 2., pp. R163-R169.

Li et al. "Inferring Gene Transcriptional Modulatory Relations: A Genetical Genomics Approach." 2005 Hum. Mol. Genet., vol. 14(9), pp. 1119-11125.

Li et al. Construction of Standard Human Transcript Dataset Based on RefSeq and Human Genome Sequence Database. 2006, Yi Chuan., vol. 28, pp. 329-333.

Lifton, R.P. "Genetic Dissection of Human Blood Pressure Variation: Etymology and Strategic Intentions." 2004-2005 Harvey Lect., vol. 100, pp. 71-101.

Lunter et al. "Genome-wide Identification of Human Functional DNA Using a Neutral Indel Model." 2006, PLoS Comput. Biol., vol. 2, pp. e5.

Mantel et al. "Statistical Aspects of the Analysis of Data from Retrospective Studies of Disease." 1959, J. Natl. Cancer Inst., vol. 22(4), pp. 719-748.

Margulies et al. "Genome Sequencing in Microfabricated High-density Picolitre Reactors." 2005, Nature, vol. 437, pp. 376-380.

Meyer-Lindenberg et al. "Intermediate Phenotypes and Genetic Mechanisms of Psychiatric Disorders." 2006, Nat. Rev. Neurosci., vol. 7(1), pp. 818-827.

Minoretti et al. "The T393C Polymorphism of the GNAS1 Gene is Associated with Deficit Schizophrenia in an Italian Population Sample." 2006, Neurosci. Lett., vol. 397(1-2), pp. 159-163 (Abstact Only).

Mullikin et al. "An SNP Map of Human Chromosome 22." 2000, Nature, vol. 407, pp. 516-520.

Nakano et al. "Selection for Thermodynamically Stable DNA Tetraloops Using Temperature Gradient Gel Electrophoresis Reveals Four Motifs: d(cGNNAg), d(cGNABg), d(cCNNGg), and d(gCN-NGc)." 2002, Biochemistry, vol. 41, pp. 14281-14292.

Ng et al. "Multiplex Sequencing of Paired-end Ditags (MS-PET): A Strategy for the Ultra-high-throughput Analysis of Transcriptomes and Genomes." 2006, Nucleic Acids Res., vol. 34(12), pp. e84.

O'Connell et al. "PedCheck: A Program for Identification of Genotype Incompatibilities in Linkage Analysis." 1998, Am. J. Hum. Genet., vol. 63(1), pp. 259-266.

Pae et al. "Glutathione S-transferase M1 Polymorphism May Contribute to Schizophrenia in the Korean Population." 2004, Psychiatr. Genet., vol. 14(3), pp. 147-150 (Abstract Only).

Parsons et al. "Colorectal Cancer: Mutations in a Signalling Pathway." 2005, Nature, vol. 436(7052), p. 792 (Abstact Only).

Paz et al. "Increased Expression of Activity-Dependent Genes in Cerebellar Glutamatergic Neurons of Patients with Schizophrenia." 2006, Am. J. Psychiatry, vol. 163(10), pp. 1829-1831.

Peccoud et al. "Parameterization of a Nonlinear Genotype to Phenotype Map Using Molecular Networks." 2005, Pac. Symp. Biocomput., pp. 284-295.

Peccoud et al. "The Selective Values of Alleles in a Molecular Network Model Are Context Dependent." 2004, Genetics, vol. 166, pp. 1715-1725.

Pfenniger et al. "Regulation of Membrane Expression at the Nerve Growth Core." 2003, J. Cell. Sci., vol. 116(Pt. 7), pp. 1209-1217.

Prinout from Bugzilla webpager regarding Description of Bugzilla Server Software, available at http://www.bugzilla.org (retrieved Jul. 20, 2009).

Prinout of webpage for Nathional Human Genome Research Institute, Reaffirmation and Extension of NHGRI Rapid Data Release (Feb. 2003), available http://www.genome.gov/10506537 (retrieved Jul. 20, 2009).

Printout from AccuRev webpage, available at http://www.accurev.com/accurev-scm.html (retrieved Jul. 20, 2009).

Printout from Applied Biosystems Webpage regarding the SOLiD System: Next-Generation Sequencing, available at http://www3.appliedbiosystems.com/AB_Home/applicationstechnologies/SOLiDSystemSequencing/index.htm (retrieved Jul. 20, 2009).

Printout from Biojava webpage regarding the Biojava Project, available http://www.biojava.org (retrieved Jul. 20, 2009).

Printout from ClinicalTrials.gov webpage, available at http://clinicaltrials.gov/ (retrieved Jul. 20, 2009).

Printout from GMOD Webpage, Welcome to GMOD (Generic Model Organism Database), available at http://www.gmod.org (retrived on Jul. 20, 2009).

Printout from NCBI / NIH database regarding index of *Homo sapiens* genomes, retrieved Jul. 2, 2009 and available at ftp://ftp.ncbi.nih.gov/genomes/H_sapiens/ARCHIVE/BUILD.36.2/.

Printout from NIH Grants Webpage regarding Deep Sequencing and Haplotype Profiling of Mental Disorders, available at http://grants.nih.gov/grants/guide/pa-files/PA-07-209.html (retrieved Jul. 20, 2009).

Printout from NIH Neuroscience Microarray Consortium webpage regarding project perro-affy-human-186940, available at http://arrayconsortium.tgen.org/np2/viewProject.do?action=viewProject&projectId=186940 (retrieved Jul. 20, 2009).

Printout from the Sanger Institute regarding Sequencing *Streptococcus suis*, available at http://www.sanger.ac.uk/Projects/S_suis (retrieved Jul. 20, 2009).

Printout from webpage for Center for Collaborative Genetic Studies on Mental Disorders, available at http://nimhgenetics.org (retrieved Jul. 20, 2009).

Printout of webpage for National Human Genome Research Institute, Human Medical Sequencing Program and Current Initiatives, available at http://www.genome.gov/15014882 (retrieved Jul. 20, 2009).

Pruitt et al. "NCBI Reference Sequence (RefSeq): A Curated Nonredundant Sequence Database of Genomes, Transcripts, and Proteins." 2005, Nucleic Acids Res., vol. 33, pp. D501-D504.

Rampersaud et al. "Power Calculations for Likelihood Ratio Tests for Offspring Genotype Risks, Maternal Effects, and Parent-of-origin (POO) Effects in the Presence of Missing Parental Genotypes when Unaffected Siblings are Available." 2007, Genet. Epidemiol., vol. 31(1), pp. 18-30.

Ranjekar et al. "Decreased Antioxidant Enzymes and Membrane Essential Polyunsaturated Fatty Acids in Schizophrenic and Bipolar Mood Disorder Patients." 2003, Psychiatry Res., vol. 121(12), pp. 109-122 (Abstract Only).

Redon et al. "Global Variation in Copy Number in the Human Genome." 2006, Nature, vol. 444(7118), pp. 444-454.

Reiner et al. "Identifying Differentially Expressed Genes Using False Discovery Rate Controlling Procedures." 2003, Bioinformatics, vol. 19(3), pp. 368-375.

Rigoutsos et al. "Short Blocks from the Noncoding Parts of the Human Genome Have Instances within Nearly All Known Genes and Relate to Biological Processes." 2006, PNAS, vol. 103(17), pp. 6605-6610.

Risch, N. "Linkage Strategies for Genetically Complex Traits. I. Multilocus Models." 1990, Am. J. Hum. Genet., vol. 46(2), pp. 222-228.

Robertson et al. "5-Oxoprolinuria in an Adolescent with Chronic Metabolic Acidosis, Mental Retardation, and Psychosis." 1991, J. Pediatr., vol. 118(1), pp. 92-95 (Abstact Only).

Roffman et al. "Neuroimaging-genetic Paradigms: A New Approach to Investigate the Pathophysiology and Treatment of Cognitive Deficits in Schizophrenia." 2006, Harv. Rev. Psychiatry, vol. 14(2), pp. 78-91 (Abstact Only).

Rogaeva et al. "The Neuronal Sortilin-related Receptor SORL1 is Genetically Associated with Alzheimer Disease." 2007, Nat. Genet., vol. 39(2), pp. 168-177.

Sabatti et al. "False Discovery Rate in Linkage and Association Genome Screens for Complex Disorders." 2003, Genetics, vol. 164(2), pp. 829-833.

Saha et al. "Using the Transcriptome to Annotate the Genome." 2002, Nature Biotchnol., vol. 20, pp. 508-512.

Schadt et al. "A Comprehensive Transcript Index of the Human Genome Generated Using Microarrays and Computational Approaches." 2004, Genome Biol., vol. 5, pp. R73.

Shai, R.M. "Microarray Tools for Deciphering Complex Diseases." 2006, Front. Biosci., vol. 11, pp. 1414-1424 (Abstact Only).

Sharov et al. "Genome-wide Assembly and Analysis of Alternative Transcripts in Mouse." 2005, Genome Res., vol. 15, pp. 748-754.

Sharp et al. "The Future of Genomic Profiling of Neurological Diseases Using Blood." 2006, Arch. Neurol., vol. 63(11), pp. 1529-1536.

Shendure et al. "Accurate Multiplex Polony Sequencing of an Evolved Bacterial Genome." 2005, Science, vol. 309(5741), pp. 1728-1732.

Shinkai et al. "No Association Between the Pro197Leu Polymorphism in the Glutathione Peroxidase (GPX1) Gene and Schizophrenia." 2004, Psychiatr. Genet., vol. 14(3), pp. 177-180 (Abstact Only).

Sjoblom et al. "The Consensus Coding Sequences of Human Breast and Colorectal Cancers." 2006, Science, vol. 314, pp. 268-274.

Sriskandan et el. "Invasive Disease and Toxic Shock due to Zoonotic *Streptococcus suis*: An Emerging Infection in the East?" 2006, PLoS Med., vol. 3(5), pp. e187.

Storey et al. "Statistical Significance for Genomewide Studies." 2003, PNAS, vol. 100(16), pp. 9440-9445.

Stranger et al. "Relative Impact of Nucleotide and Copy Number Variation on Gene Expression Phenotypes." 2007, Science, vol. 315(5813), pp. 848-853.

Sugarbaker et al. "Transcriptome Sequencing of Malignant Pleural Mesothelioma Tumors." 2007, PNAS, vol. 105(9), pp. 3521-3526.

Terpstra et al. "Validation of Glutathione Quantitation from STEAM Spectra Against Edited 1H NMR Spectroscopy at 4T: Application to Schizophrenia." 2005, MAGMA, vol. 18(5), pp. 279-282 (Abstact Only).

Thomas et al. "Coding Single-nucleotide Polymorphisms Associated with Complex vs. Mendelian Disease: Evolutionary Evidence for Differences in Molecular Effects." 2004, PNAS, vol. 101(43), pp. 15398-15403.

Tosic et al. "Schizophrenia and Oxidative Stress: Glutamate Cysteine Ligase Modifier as a Susceptibility Gene." 2006, Am. J. Hum. Genet., vol. 79(3), pp. 586-592.

Van Steen et al. "PBAT: A Comprehensive Software Package for Genome-Wide Association Analysis of Complex Family-Based Studies." 2005, Hum. Genomics, vol. 2(1), pp. 67-69 (Abstact Only).

Velculescu et al. "What Transcripts are Found in a Human Cell?" 2001, Genome Biol., vol. 1, pp. R31.

Walther et al. "Synthesis of Serotonin by a Second Tryptophan Hydroxylase Isoform." 2003, Science, vol. 299(5603), pp. 76.

Wang et al. "Mutational Analysis of the Tyrosine Phosphatome in Colorectal Cancers." 2004, Science, vol. 304(5674), pp. 1164-1166.

Weller et al. "A New Approach to the Problem of Multiple Comparisons in the Genetic Dissection of Complex Traits." 1998, Genetics, vol. 150(4), pp. 1699-1706.

Wendl, M.C. "A General Coverage Theory for Shotgun DNA Sequencing." 2006, J. Comput. Biol., vol. 13(6), pp. 1177-1196.

Whalley et al. "Functional Imaging as a Predictor of Schizophrenia." 2006, Biol. Psychiatry, vol. 60(5), pp. 454-462 (Abstact Only).

Wigginton et al. PEDSTATS; Descriptive Statistics, Graphics and Quality Assessment for Gene Mapping Data. 2005, Bioinformatics, vol. 21(16), pp. 3445-3447.

Wong et al. "A Comprehensive Analysis of Common Copy-number Variations in the Human Genome." 2007, Am. J. Hum. Genet., vol. 80(1), pp. 91-104.

Wu et al. "GMAP: A Genomic Mapping and Alignment Program for mRNA and EST Sequences." 2005, Bioinformatics, vol. 21, pp. 1859-1875.

Yao et al. "Human Plasma Glutathione Peroxidase and Symptom Severity in Schizophrenia." 1999, Biol. Psychiatry, vol. 45(11), pp. 1512-1515 (Abstact Only).

Yao et al. "Reduced Status of Plasma Total Antioxidant Capacity in Schizophrenia." 1998, Schizophr. Res., vol. 32(1), pp. 1-8 (Abstact Only).

Yao et al. "Altered Glutathione Redox State in Schizophrenia." 2006, Dis. Markers., vol. 22(1-2), pp. 83-93.

Zhang et al. "Antioxidant Enzymes and Lipid Peroxidation in Different Forms of Schizophrenia Treated with Typical and Atypical Antipsychotics." 2006, Scizophr. Res., vol. 81(2-3), pp. 291-300 (Abstact Only).

Zhang et al. "Functional Polymorphisms of the Brain Serotonin Synthesizing Enzyme Tyrosine Hydroxylase-2." 2006, Cell Mol. Life Sci., vol. 63(1), pp. 6-11.

Zhang et al. "The Gene for the Muted (mu) Mouse, a Model for Hermansky-Pudlak Syndrome, Defines a Novel Protein which Regulates Vesicle Trafficking." 2002, Hum. Mol. Genet., vol. 11(6), 697-706.

Zhang et al. "A Greedy Algorithm for Aligning DNA Sequences." 200, J. Comput. Biol., vol. 7, pp. 203-214, 2000.

Zhuo et al. "Modern Origin of Numerous Alternatively Spliced Human Introns from Tandem Arrays." 2007, Pnas, vol. 104(3), pp. 882-886.

Zori et al. "Phenocopy versus Genocopy." 1991, Am. J. Med. Genet., vol. 40, pp. 248-249 (Abstact Only).

International Search Report and Written Opinion issued Feb. 2, 2011 for PCT/US10/53875, which was filed on Oct. 22, 2010 and published as WO 2011/050341 on Apr. 28, 2011 (Applicant—National Center for Genome Resources; Inventors—Kingsmore et al.).

* cited by examiner

FIG. 6

| Select Case(s) | Search by gene name |
|---|---|
| SID376 | starts with [dropdown] [_____] |
| SID524 | |
| SID557 | Restrict to Sanger genes ☐ |
| SID558 | |
| SID559 | Restrict to Affymetrix genes ☐ |
| SID816 | |

Restrict search to genes with associated read count >= [____] and <= [____]

[Find Genes]
[Reset]

A. Restrict where at least [____] reads call variant

B. Restrict where at least [____] reads cover position

C. Restrict where at least [____] % of reads in position show variant

Note that A / B = C %

Restrict by associated variant type
☐ SNP    ☐ non-synonymous SNP    ☐ in/del

Restrict where variant in transcript coding region (CDS) ☐

Restrict where variant causes premature stop codon ☐

FIG. 10B

```
Query   61  CCGCAGGCTCAAatcgaatgaatgaacttcttcatctgtgaaaaa 110
            |||| ||||||||||||||||||||||||||||||||||||||||
Subject 2215 CAGCAGGCTCAAatcgaatgaacttcttcatctgtgaaaaa 2264
```

FIG. 10C

```
Query    1  CCGCCCCTAGTCTCCCACCCCTTCCCCCGTAGTGACCAATTCCTATCTCTTCCCTCT  60
            ||||||||||||||||||||||||||||||||||||||||||||||||||||||||
Chr19 5611708 CCGCCCCTAGTCTCCCACCCCTTCCCCCGTAGTGACCAATTCCTATCTCTTCCCTCT 5611649

Query   61  CCGCAGGCTCAAATCGAATGAATGTGAACTTCTTCATCTGTGAAAAA 110
            |||||||||||||||||||||||||||||||||||||||||||||||
Chr19 5611648 CCGCAGGCTCAAATCGAATGAATGTGAACTTCTTCATCTGTGAAAAA 5611599
```

```
                    G   Q   Q   Q   A
     CGCCGCCCAC GCAGCAGGGA CAGCAGCAGG CAagtgggaa ttgccaccct cctcctcctc
 541
 601 ctttctcctt ccaaccccg  gccaccgtcc atcctgcctt agtgggtagc gccggaaacc
 661 ccttccctg  cgggtgtgc  ccttgatgcc tgcagcgggg gccgtgtggc cggaggtctc
 721 cgggagtccc cacgcaccgc cagggaagca ttcgctgggt ccagaggtta aacgaagagg
 781 cctccctgcg ccggctgctt gttcctgtgt gccgctgtcg tgatgctggg gagcgctgag
 841 actcgcaggc gggacttctg aactgctggg gagtcggggg gcaggcagac agcgcggacg
 901 gtgggcaccg gcccgcccgc ccactactgc tcacaatctg gccacttggg aagaaaacgt
 961 ctattttttc cccttctctg catcactttt ttggtttttg ttctttttat tctttttattt
1021 tttaaaccca tgatctttt  tcctgtgtcc aagtgactgt gttgcaggcg gccggctct
1081 ggcaggact  ggtggggacg cggggagcgg cccccgcccg tgccccgccg ggctcagcct
1141 cccatgcgct cgcgcttgcc tgtgtctgt  gcttgtctgt gaagtgggcg tgaagatcgt
1201 tgccaccttc caacctacct cacaggggtg ttgtggggac accatgatct ctggattgtt
1261 catgtcgttg tgctgcgccg ggagccaccg ccctccggag acaggccagc tcccctacga
1321 ccctagcgcc tccgcccctc gcggccccct cccgcgagtc tcctctcttc cctcctctc
1381 catcagggag cacgtgact  tcagccgagc gcagccaggt ttgggagggg gcttcctgac agttaacaag
1441 cacgtccttc cagcctcagc cagcagggct tcagcgagtc cagcgcaggt gcttcctggc ccccccacg
1501 gtgttccag  cccctcctc  ttccgcccc  tagtcctcca cccttccctc ccgtaggac
      Q  F  L  S   L  P  S   P  Q  A   Q stop
1561 caattcctat ctcttccctc tccgcaggct CAATGAatcg aatgaatgtg aacttcttca .........
```

METHODS AND SYSTEMS FOR MEDICAL SEQUENCING ANALYSIS

CROSS REFERENCE

This application claims priority to U.S. Provisional Application No. 60/919,435 filed Mar. 22, 2007, herein incorporated by reference in its entirety.

BACKGROUND

Medical sequencing is a new approach to discovery of the genetic causes of complex disorders. Medical sequencing refers to the brute-force sequencing of the genome or transcriptome of individuals affected by a disease or with a trait of interest. Dissection of the cause of common, complex traits is anticipated to have an immense impact on the biotechnology, pharmaceutical, diagnostics, healthcare and agricultural biotech industries. In particular, it is anticipated to result in the identification of novel diagnostic tests, novel targets for drug development, and novel strategies for breeding improved crops and livestock animals. Medical sequencing has been made possible by the development of transformational, next generation DNA sequencing instruments, developed by 454 Life Sciences/Roche Diagnostics, Applied Biosystems/Agencourt, Illumina/Solexa and Helicos, these instruments are anticipated to increase the speed and throughput of DNA sequencing by 3000-fold (to 2 billion base pairs of DNA sequence per instrument per experiment).

Common, conventional approaches to the discovery of the genetic basis of complex disorders include the use of linkage disequilibrium to identify quantitative trait loci in studies of multiple sets of affected pedigrees, candidate gene-based association studies in cohorts of affected and unaffected individuals that have been matched for confounding factors such as ethnicity, and whole genome genotyping studies in which associations are sought between linkage disequilibrium segments (based upon tagging SNP genotypes or haplotypes), and diagnosis in cohorts of affected and unaffected individuals that have been matched for confounding factors.

These methods are based on the assumption that complex disorders share underlying genetic components (i.e. are largely genetically homogeneous). In other words, while complex diseases result from the cumulative impact of many genetic factors, those factors are largely the same in individuals. While this assumption has met with some success, there are numerous cases where this commonality has failed. Progress in dissecting the genetics of complex disorders using these approaches has been slow and limited. Software systems for DNA sequence variant discovery operating under this assumption are inadequate for next-generation DNA sequencing technologies that feature short read lengths, novel base calling and quality score determination methods, and relatively high error rates.

SUMMARY

Disclosed are methods of identifying elements associated with a trait, such as a disease. The methods can comprise, for example, identifying the association of a relevant element (such as a genetic variant) with a relevant component phenotype (such as a disease symptom) of the trait, wherein the association of the relevant element with the relevant component phenotype identifies the relevant element as an element associated with the trait, wherein the relevant component phenotype is a component phenotype having a threshold value of severity, age of onset, specificity to the trait or disease, or a combination, wherein the relevant element is an element having a threshold value of importance of the element to homeostasis relevant to the trait, intensity of the perturbation of the element, duration of the effect of the element, or a combination.

The disclosed methods are based on a model of how elements affect complex diseases. The disclosed model is based on the existence of significant genetic and environmental heterogeneity in complex diseases. Thus, the specific combinations of genetic and environmental elements that cause disease vary widely among the affected individuals in a cohort. Implications of this model include:

- Comparisons of candidate variant allele frequencies between affected and unaffected cohorts that do not identify statistical differences in a complex disease do not exclude that variant from causality in individuals within the affected cohort.
- Experimental designs based upon comparisons of candidate variant allele frequencies between affected and unaffected cohorts, even if undertaken on a large scale, will fail to disclose causal variants in situations where there is a high degree of heterogeneity among individuals in causal elements.
- Statistical methods will not give detailed information on a specific individual, which is a key need in personalized medicine and medical sequencing.

The disclosed model is an effective, general experimental design and analysis approach for the identification of causal variants in common, complex diseases by medical sequencing. The model can utilize various approaches including, but not limited to, one or more of the following:

1. Evaluating associations with component phenotypes (Cp) rather than diseases (D): a "candidate component phenotype" approach.
2. Including severity (Sv) and duration (t) when evaluating associations with Cp.
3. Evaluating associations in individuals and subsets of cohorts in addition to cohorts.
4. Evaluating associations in single pedigrees rather than integrating results of several pedigrees.
5. Including intensity of the perturbation (I) and t in associations of elements (E). For medical sequencing, this can mean, for example, focusing on non-synonymous variants with large negative BLOSUM scores. For medical sequencing this has the further implication that evaluations of the transcriptome sequence and abundance in affected cells or tissues is likely to provide greater signal to noise than the genome sequence.
6. Following cataloging of E, I and t, assemble E into a minimal set of physiologic or biochemical pathways or networks (P). Seek associations of resultant P with Cp.
7. Seeking unbiased approaches to selection of Cp. For example, seek associations with Cp that are suggested by P. Further, Cp can vary from highly specific to general. Initial associations with Cp can be as specific as possible based upon P.

The disclosed model and the disclosed methods based on the model can be used to generate valuable and useful information. At a basic level, identification of elements (such as genetic variants) that are associated with a trait (such as a disease or phenotype) provides greater understanding of traits, diseases and phenotypes. Thus, the disclosed model and methods can be used as research tools. At another level, the elements associated with traits through use of the disclosed model and methods are significant targets for, for example, drug identification and/or design, therapy identification and/or design, subject and patient identification, diagnosis, prognosis as they relate to the trait. The disclosed model and methods will identify elements associated with traits that are more significant or more likely to be significant to the genesis, maintenance, severity and/or amelioration of the trait. The display, output, cataloging, addition to databases and the like of elements associated with traits and the association of elements to traits provides useful tools and information to those identifying, designing and validating drugs, therapies, diagnostic methods, prognostic methods in relation to traits.

It should be understood that elements (such as genetic variants) identified using the disclosed model and methods can be part of other components or features (such as the gene in which the genetic variant occurs) and/or related to other components or features (such as the protein or expression product encoded by the gene in which the genetic variant occurs or a pathway to which the expression product of the gene belongs). Such components and features related to identified elements can also be used in or for, for example, drug identification and/or design, therapy identification and/or design, subject and patient identification, diagnosis, prognosis as they relate to the trait. Such components and features related to identified elements can also be targets for identifying, designing and validating drugs, therapies, diagnostic methods, prognostic methods in relation to traits and/or can provide useful tools and information to those identifying, designing and validating drugs, therapies, diagnostic methods, prognostic methods in relation to traits.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems.

FIG. 6 shows an example of a sequence query interface.

FIG. 7 illustrates the identification of a coding domain (CD) SNP in the α subunit of the Guanine nucleotide-binding stimulatory protein (GNAS) using the disclosed methods.

FIGS. 10A-C illustrate an example of a novel splice isoform identified with GMAP by an apparent SNP at the penultimate base of an alignment. FIG. 10B comprises SEQ ID NO: 1 (Query 61) and SEQ ID NO:2 (Subject 2215). The top part of FIG. 10C comprises SEQ ID NO: 3 (Query 1) and SEQ ID NO: 4 (Chr19 5611708). The bottom part of FIG. 10C comprises SEQ ID NO: 5 (Query 61) and SEQ ID NO: 6 (Chr19 5611648).

FIG. 11 illustrates an example of a novel splice isoform (SEQ ID NO: 7) identified with GMAP by an apparent SNP at the penultimate base of an alignment.

FIG. 12 illustrates a GMAP alignment of read D9VJ59F02JQMRR (nt 1-109, top, SEQ ID NO: 8) from SID 1438, to SYNCRIP (NM_006372.3, bottom, SEQ ID NO: 9) showing a nsSNP at nt 30 (yellow, a1384g) and a novel splice isoform that omits an 105-bp exon and maintains frame.

DETAILED DESCRIPTION

Figure 1:
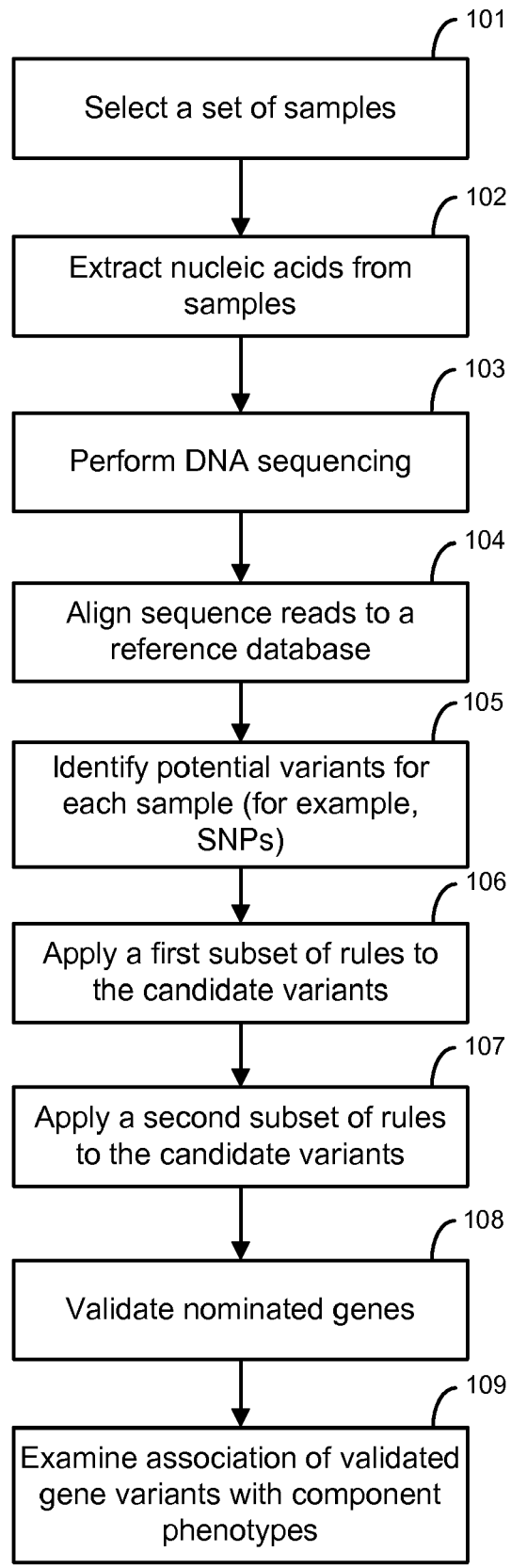
FIG. 1 is a block diagram illustrating an exemplary medical sequencing method utilizing, for example, 454 pyrosequencing and substitution variants in transcriptome sequence data.

Before the present methods and systems are disclosed and described, it is to be understood that the methods and systems are not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

The present methods and systems may be understood more readily by reference to the following detailed description of preferred embodiments and the Examples included therein and to the Figures and their previous and following description.

I. Model

Genetic heterogeneity is a potential cause for the lack of replication among studies of complex disorders. The prevailing assumption has been that there is sufficient homogeneity in causal elements in individuals affected by a common, complex disease that comparisons of candidate variant allele frequencies between affected and unaffected cohorts will identify differences based on some inferential measure. This assumption was borne out of successes in studies of this type. For example, HLA haplotypes show association with several common, complex diseases.

However, to uncover the causative genetic components relevant to individual, personalized medicine, it is necessary to move from the statistical to the determinate. This is also necessary if, in complex diseases, there is insufficient homogeneity of causal elements among affected individuals to enable detection of statistical differences. The disclosed model is based on the existence of significant genetic and environmental heterogeneity in complex diseases. Thus, the specific combinations of genetic and environmental elements that cause disease vary widely among the affected individuals in a cohort. Implications of this model include:

- Comparisons of candidate variant allele frequencies between affected and unaffected cohorts that do not identify statistical differences in a complex disease do not exclude that variant from causality in individuals within the affected cohort.
- Experimental designs based upon comparisons of candidate variant allele frequencies between affected and unaffected cohorts, even if undertaken on a large scale, will fail to disclose causal variants in situations where there is a high degree of heterogeneity among individuals in causal elements.
- Statistical methods will not give detailed information on a specific individual, which is a key need in personalized medicine and medical sequencing.

The disclosed model is based upon genetic, environmental and phenotypic heterogeneity in common, complex diseases. The model notes that multiple elements ($E_1 \ldots E_n$) can be involved in the causality of a common, complex disease (D). These elements can be genetic (G) factors, environmental (E) factors or combinations thereof. The traditional approach is to decompose G×E into genetic factors, G (which can be further decomposed into additive "a", dominance "d", and epistatic "e" factors), an environment factor "E", their non-linear interaction "G×E", and a noise term "epsilon" (always present in every experiment and every data set). The genetic decomposition can be important because additive genetic variance is heritable, while dominance and epistatic variance are reconstituted each generation as a result of each individual's unique genome. It is further noted that elements can have heterogeneous contributions to phenotypes. Thus elements can be either deleterious (predisposition) or advantageous (protection) in terms of disease development. Further, elements can vary in expressivity and penetrance. It is further noted that some elements can have very specific effects whereas others are pleiotropic. For example, a variant in an enzyme may affect only a single biochemical pathway whereas a variant in a transcription factor may affect many pathways. These additive and nonadditive effects can be context dependent. Thus, the model can view D as a phenomenon that broadly describes the outward phenotype of the combinatorial consequence of allelic and environmental variations. The disclosed model utilizes a more general approach that can seek associations in individuals. It is further noted that the magnitude of the effect of an individual element can be dependent upon at least three variables:

1. The importance of that particular element for maintenance of homeostasis (H) relevant to the disease (D). Some elements will have minor importance, while others will have major importance. For example, the knockout of a specific gene in a mouse can result in a phenotype that varies between no effect and embryonic lethality. Thus each element ($E_1 \ldots E_n$) has a specific, contributory role as part of the cause of, or protection against, a complex disease ($H_1 \ldots H_n$).

2. The intensity of the perturbation of that element (I). For genetic elements, the intensity of the perturbation is dependent upon the type of variant, the number of copies of variant element or the magnitude of gene expression difference. The types of genetic variant include synonymous (which may be further categorized into regulatory and non-regulatory SNP and/or coding and noncoding SNP) and non-synonymous SNPs (which may be further categorized by scores such as BLOSUM score), indels (coding domain and non-coding domain), and whole or partial gene duplications, deletions and rearrangements. The number of copies of a variant genetic element may reflect homozygosity, heterozygosity or hemizygosity. Thus each element ($E_1 \ldots E_n$) in an individual has a specific and variable intensity ($I_1 \ldots I_n$).

3. The duration of the effect of the element (t). Environmental elements may be acute or chronic in nature. An example is occurrence of skin cancer following acute exposure to ultraviolet radiation while sunbathing versus continuous exposure through an outdoor occupation. Genetic elements may also be acute or chronic in nature, since many genes are not constitutively expressed but rather under transcriptional and/or post-transcriptional regulation. Therefore, a variant genetic element may not necessarily be expressed in an individual (called "expressivity" for within an individual; "penetrance" for occurrence in a population). Thus each element ($E_1 \ldots E_n$) in an individual has a specific and variable duration of effect ($t_1 \ldots t_n$) that may not be constant but that may be a function of the environment.

Thus, for any given element $E_i$, the contribution towards causality in a disease can be a function, f, of these three factors. Thus:

$$E_i = f(H_i, I_i, t_i)$$

and similarly the disease itself can be a function, g, of these n elements:

$$D = g(E_{1 \ldots n})$$

This variability has several implications. For example, while in any individual, there are likely to be a finite number of elements that cause a common complex disease, in an outbred population there exist an extraordinarily large number of possible combinations of $E_1 \ldots E_n$ that can lead to that disease. In turn, while the variance explained by a given element ($E_x$) in an individual could certainly be large (i.e. 5-20%), the variance between that element and a disease in an outbred population is most likely to be very small (i.e. 0.1%). Thus, associations between individual element frequencies ($E_x$) and occurrence of a common, complex disease in an outbred population can lead to false negative results.

Different elements in any individual can lead to a given effect. Thus, both genocopies and envirocopies exist.

Values of t and I can have significant impact on E. Thus, strategies that evaluate gene candidacy based upon a tagged SNP (which may ignore the variables t and I) can yield false positive results.

Sampling of multiple individuals within a single pedigree can be highly informative since the number of combinations of possible elements is greatly decreased by laws of inheritance.

While in any individual pedigree there can be a finite number of elements that cause a common complex disease, in a set of unrelated pedigrees there exist an extraordinarily large number of possible combinations of $E_1 \ldots E_n$ that can lead to that disease. In turn, while the variance explained by a given element ($E_x$) in an individual pedigree could certainly be large, the variance between that element and a disease in a set of unrelated pedigrees is most likely to be very small. Thus associations between individual element frequencies ($E_x$) and occurrence of a common, complex disease in sets of unrelated pedigrees can lead to false negative results.

Another implication includes phenotypic heterogeneity in common, complex diseases. The model notes that conventional definitions of common, complex diseases can represent a combination of multiple component phenotypes ($Cp_1 \ldots Cp_n$), also known as "endophenotypes", that have been rather arbitrarily assembled through years of medical experience and consensus. These component phenotypes can be symptoms, signs, diagnostic values, and the like.

Given the informal process of inclusion or exclusion of Cp in a common, complex disease, the disclosed model notes that individual Cp may not always be present in any individual case of a common, complex disease (i.e. phenocopies exist). Some Cp will be present in the vast majority of cases (commonly referred to as pathognomonic features), whereas others will be present in only a few. Further, some Cp are pleiotropic (i.e. present in multiple common, complex diseases). An example is elevated serum or plasma C reactive protein. Other Cp are unique to a single D. An example is auditory hallucinations. Most Cp are anticipated to fit somewhere between these extremes (such as giant cell granulomas on histology).

The model further notes that for any D, the conventional cluster of Cp that are used for disease definition is inexact. It does not include all relevant Cp—but rather a subset that are currently known, established or included in the description of that disease. Furthermore, some Cp may be incorrectly included in the definition of that D. Other Cp may have been incorrectly omitted. Thus each Cp ($Cp_1 \ldots Cp_n$) can have a specific and individual value in the description of the presence of a common, complex disease (D). The set of Cp that are used for traditional diagnosis may not be complete or completely correct.

An implication of the model is that comparisons of candidate variant allele frequencies between affected and unaffected cohorts as defined by D that do not identify statistical differences in a common, complex disease do not exclude that variant from causality in Cp in individuals within the affected cohort. A further implication is that experimental designs based upon comparisons of candidate variant allele frequencies between affected and unaffected cohorts as defined by D, will be subject to false negative errors. A more general approach is to seek associations with Cp.

The model further notes that the magnitude of the effect of an individual Cp can be dependent upon two additional variables. One of the variables is the severity of the perturbation (Sv) of that Cp. For example, one might have a thrombocytopenia of $100/mm^3$ or $50,000/mm^3$ of blood. Auditory hallucinations may have occurred once a year or many times per hour. Thus each Cp ($Cp_1 \ldots Cp_n$) in an individual with disease has a specific and variable severity ($Sv_1 \ldots Sv_n$).

The other variable that an individual Cp can be dependent upon is the age of onset (A) of that Cp. For example, dementia may occur in young persons or in the elderly. We know that the pathophysiology of dementia in young people is frequently brain tumor. In elderly persons, it is frequently Alzheimer's disease or secondary to depression. Thus each Cp ($Cp_1 \ldots Cp_n$) in an individual has a specific and variable time to onset ($A_1 \ldots A_n$).

Thus, for any given Cp, an effective definition can be a function, h, of these three factors. Thus:

$$D = h(Cp_{1\ldots n}, Sv_{1\ldots n}, A_{1\ldots n})$$

and therefore:

$$D = g(E_{1\ldots n}) = h(Cp_{1\ldots n}, Sv_{1\ldots n}, A_{1\ldots n})$$

thus mapping causal elements to phenotypic expression.

Cp heterogeneity can have several other implications including that attempts to find causal elements in studies predicated on the traditional definitions of common, complex diseases are likely to be unsuccessful due to the informal methods whereby Cp have been assembled into conventional definitions and by the weightings of Sv or t (if any) by which Cp have empirically been weighted. Attempts to find solutions for individual Cp are more likely to be successful. Furthermore, attempts to find solutions for individual Cp are more likely to be successful if Sv and t values are measured and cut-off values defined prospectively.

Additionally, the inclusion/exclusion of traditional Cp are biased by medical experience and consensus. Unbiased Cp (suggested by experimentally-derived values of E or physiologic or biochemical pathways or networks (P)) are more likely to show associations. Molecular Cp, such as gene or protein expression profiles, are an example of phenotypes that are experimentally-derived and likely to be intermediary between gene sequences and organismal traits.

Another implication is the convergence of elements into networks and pathways. Genetic and environmental heterogeneity in common, complex disorders can be partitioned by assembly of individual E into physiologic or biochemical pathways or networks (P). This is based upon the observations that:
  a. Eukaryotic biochemistry is organized into pathways and networks of interacting elements. Very few genes act in isolation.
  b. Eukaryotic biochemistry is rather constrained.
  c. Challenges to homeostasis typically evoke stereotyped responses.

Thus, common, complex disorders are anticipated to appear stochastic or indecipherable when considered at the level of E due both to interactions with the genome and to the intrinsic heterogeneity in causality of D. However, it has been realized that heterogeneous combinations of individual E will converge into a discrete number of P. Linked, non-casual variations, in contrast, are not anticipated to converge into P.

The convergence of elements into networks and pathways is also based upon experience in analysis of gene expression profiling experiments, where many disparate transcripts are typically upregulated or downregulated in expression between two states or individuals. Lists of differentially expressed genes are typically analyzed by synthesis into perturbed networks or pathways in order to understand the principal differences.

Another implication of the model is the combination of medical sequencing data with genetic, gene and protein expression and metabolite profiling data. The analysis of medical sequencing data—a list of genes with putative, physiologically important sequence variation—can be facilitated by integrative approaches that combine medical sequencing data results with results of other approaches, such as genetic (linkage) data, gene expression profiling data and proteomic and metabolic profiling data.

The disclosed model is an effective, general experimental design and analysis approach for the identification of causal variants in common, complex diseases by medical sequencing. The model can utilize various approaches including, but not limited to, one or more of the following:
  1. Evaluating associations with component phenotypes (Cp) rather than diseases (D): a "candidate component phenotype" approach.
  2. Including severity (Sv) and duration (t) when evaluating associations with Cp.
  3. Evaluating associations in individuals and subsets of cohorts in addition to cohorts.

4. Evaluating associations in single pedigrees rather than integrating results of several pedigrees.
5. Including intensity of the perturbation (I) and t in associations of elements (E). For medical sequencing, this can mean, for example, focusing on non-synonymous variants with large negative BLOSUM scores. For medical sequencing this has the further implication that evaluations of the transcriptome sequence and abundance in affected cells or tissues is likely to provide greater signal to noise than the genome sequence.
6. Following cataloging of E, I and t, assemble E into a minimal set of physiologic or biochemical pathways or networks (P). Seek associations of resultant P with Cp.
7. Seeking unbiased approaches to selection of Cp. For example, seek associations with Cp that are suggested by P. Further, Cp can vary from highly specific to general. Initial associations with Cp can be as specific as possible based upon P.

As noted above, common complex diseases can have heterogeneous descriptions based on informal assembly of component phenotypes into the disease description. Given this heterogeneity of the features that can be ascribed to a disease, and because the principles of this model are not limited to "diseases" as that term is used in the art, the disclosed model and methods can be used in connection with "traits." The term trait, which is further described elsewhere herein, is intended to encompass observed features that may or may not constitute or be a component of an identified disease. Such traits can be medically relevant and can be associated with elements just as diseases can.

The disclosed model and the disclosed methods based on the model can be used to generate valuable and useful information. At a basic level, identification of elements (such as genetic variants) that are associated with a trait (such as a disease or phenotype) provides greater understanding of traits, diseases and phenotypes. Thus, the disclosed model and methods can be used as research tools. At another level, the elements associated with traits through use of the disclosed model and methods are significant targets for, for example, drug identification and/or design, therapy identification and/or design, subject and patient identification, diagnosis, prognosis as they relate to the trait. The disclosed model and methods will identify elements associated with traits that are more significant or more likely to be significant to the genesis, maintenance, severity and/or amelioration of the trait. The display, output, cataloging, addition to databases and the like of elements associated with traits and the association of elements to traits provides useful tools and information to those identifying, designing and validating drugs, therapies, diagnostic methods, prognostic methods in relation to traits.

Figure 2:
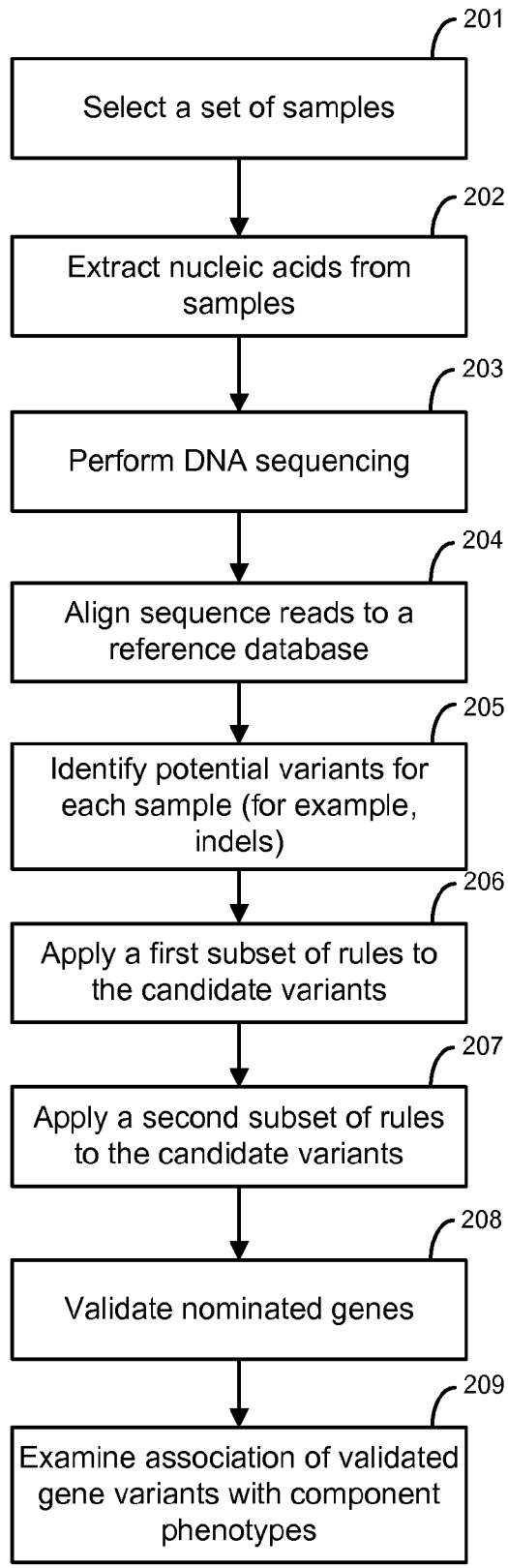
FIG. 2 is a block diagram illustrating another exemplary medical sequencing method utilizing, for example, 454 pyrosequencing and indel variants in transcriptome sequence data.

The implications of this model can be incorporated into the design of an analysis strategy such as the examples shown in FIG. 1 and FIG. 2.

FIG. 1 illustrates an exemplary medical sequencing method utilizing, for example, 454 pyrosequencing and substitution variants in transcriptome sequence data. At block 101, a discovery set of samples can be selected. At block 102, nucleic acids (for example, RNA) can be extracted from the discovery set of samples. At block 103, DNA sequencing can be performed (for example, with 454/Roche pyrosequencing). The DNA sequencing can result in the generation of sequence reads. At block 104, the sequence reads can be aligned to a reference database (for example, RefSeq with MegaBLAST). At block 105, potential variants can be identified for each sample in the discovery set (for example, SNPs). At block 106, a first subset of rules (a first filter) can be applied to identify candidate variants (for example, variants that may be associated with a trait or disease). In this example, the first subset of rules can comprise one or more of the following:
  Present in >4 sequence reads
  Present in >30% reads (assumes frequency is at least heterozygous)
  High quality score at variant base(s)
  Present in sequence reads in both orientations (5' to 3' and 3' to 5')
  Confirm read alignment to reference sequence
  Exclude reference sequence errors by alignment to a second reference database At block 107, a second subset of rules (a second filter) can be applied to the resulting candidate variants in order to prioritize the candidate variants and nominate candidate genes. In this example, the second subset of rules can comprise one or more of the following:
  Coding domain non-synonymous variant
  Severity of gene lesion (BLOSUM etc.)
  Gene congruence in >1 sample
  Network or pathway congruence in >1 sample
  Functional plausibility
  Chromosomal location congruence with known quantitative trait loci
  Congruence with other data types (e.g. gene or protein expression or metabolite information)

At block 108, the resulting nominated genes can be validated by re-sequencing the nominated genes in "Discovery" & independent "Validation" sample sets. At block 109, the association of validated gene variants with component phenotypes can be examined.

FIG. 2 illustrates another exemplary medical sequencing method utilizing, for example, 454 pyrosequencing and indel variants in transcriptome sequence data. At block 201, a discovery set of samples can be selected. At block 202, nucleic acids (for example, RNA) can be extracted from the discovery set of samples. At block 203, DNA sequencing can be performed (for example, with 454/Roche pyrosequencing). The DNA sequencing can result in the generation of sequence reads. At block 204, the sequence reads can be aligned to a reference database (for example, RefSeq with MegaBLAST). At block 205, potential variants can be identified for each sample in the discovery set (for example, indels). At block 206, a first subset of rules (a first filter) can be applied to identify candidate variants (for example, variants that may be associated with a trait or disease). In this example, the first subset of rules can comprise one or more of the following:
  Present in >4 sequence reads
  Present in >30% reads (assumes frequency is at least heterozygous)
  Absence of homopolymer bases immediately preceding indel (within 5 nucleotides)
  High quality score at variant base(s)
  Present in sequence reads in both orientations (5' to 3' and 3' to 5')
  Confirm read alignment to reference sequence
  Exclude reference sequence errors by alignment to a second reference database At block 207, a second subset of rules (a second filter) can be applied to the resulting candidate variants in order to prioritize the candidate variants and nominate candidate genes. In this example, the second subset of rules can comprise one or more of the following:
  Coding domain non-synonymous variant
  Severity of gene lesion (BLOSUM etc.)
  Gene congruence in >1 sample Network or pathway congruence in >1 sample
Functional plausibility
Chromosomal location congruence with known quantitative trait loci
Congruence with other data types (e.g. gene or protein expression information)

At block 208, the resulting nominated genes can be validated by re-sequencing the nominated genes in "Discovery" & independent "Validation" sample sets. At block 209, the association of validated gene variants with component phenotypes can be examined.

II. Exemplary Methods

Figure 3:
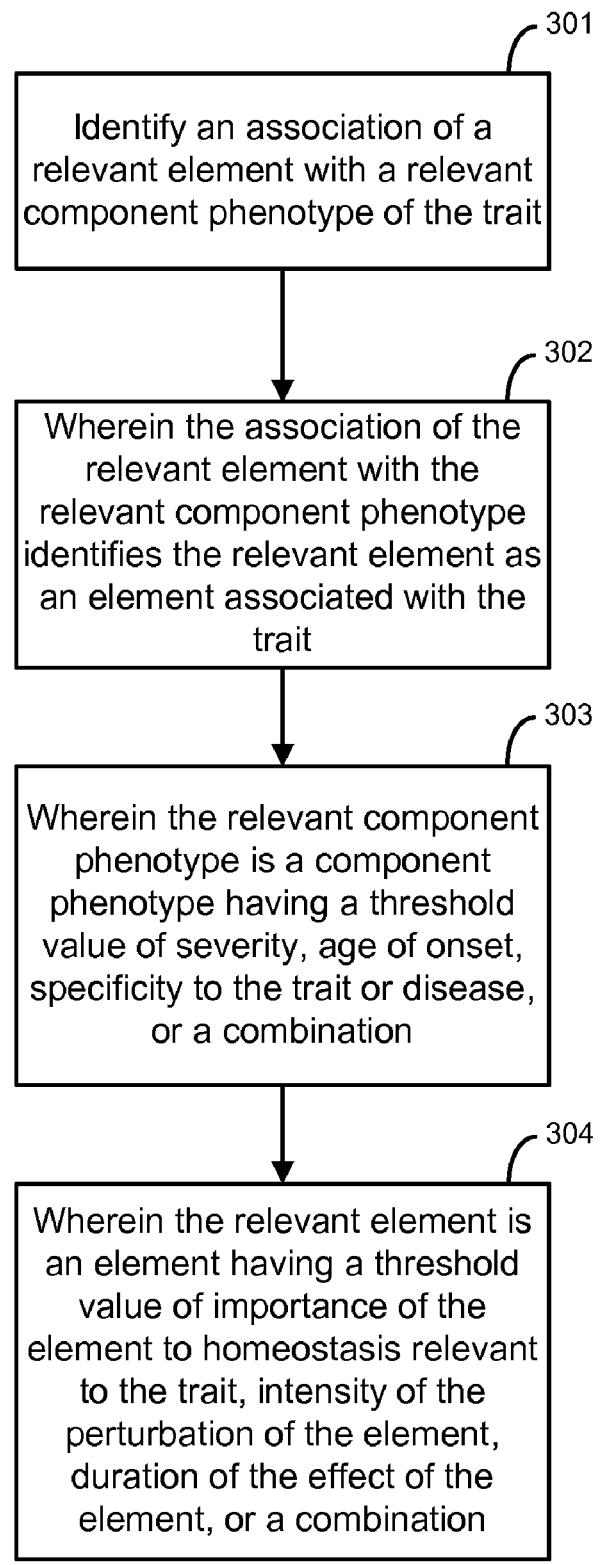
FIG. 3 is a block diagram illustrating a method of identifying elements associated with a trait, the methods can comprise identifying the association of a relevant element with a relevant component phenotype of the trait.

Provided, and illustrated in FIG. 3, are methods of identifying elements associated with a trait, the methods can comprise identifying the association of a relevant element with a relevant component phenotype of the trait at 301, wherein the association of the relevant element with the relevant component phenotype identifies the relevant element as an element associated with the trait, wherein the relevant component phenotype is a component phenotype having a threshold value of severity, age of onset, specificity to the trait or disease, or a combination at 302, wherein the relevant element is an element having a threshold value of importance of the element to homeostasis relevant to the trait, intensity of the perturbation of the element, duration of the effect of the element, or a combination at 303. It should be understood that the method can include identification of one or multiple elements, association of one or multiple elements with one or multiple traits, use of one or multiple elements, use of one or multiple component phenotype, use of one or more relevant elements, use of one or more relevant component phenotypes, etc. Such single and multiple components can be used in any combination. The model and methods described herein refer to singular elements, traits, component phenotypes, relevant elements, relevant component phenotypes, etc. merely for convenience and to aid understanding. The disclosed methods can be practiced using any number of these components as may be useful and desired.

A trait can be, for example, a disease, a phenotype, a quantitative or qualitative trait, a disease outcome, a disease susceptibility, a combination thereof, and the like. As used herein in connection with the disclosed model and methods, trait refers to one or more characteristics of interest in a subject, patient, pedigree, cohort, groups thereof and the like. Of particular interest as traits are phenotypes, features and groups of phenotypes and features that characterize, are related to, and/or are indicative of diseases and conditions. Useful traits include single phenotypes, features and the like and plural phenotypes, features and the like. A particularly useful trait is a component phenotype, such as a relevant component phenotype.

A relevant element can be an element that has a certain threshold significance/weight based on a plurality of factors. The relevant element can be an element having a threshold value of, for example, importance of the element to homeostatis relevant to the trait, intensity of the perturbation of the element, duration of the effect of the element, or a combination. The relevant element can be, for example, an element associated with one or more genetic elements associated with the trait or disease. The one or more genetic elements can be derived from, for example, DNA sequence data, genetic linkage data, gene expression data, antisense RNA data, microRNA data, proteomic data, metabolomic data, a combination, and the like. The relevant element can be a relevant genetic element. A relevant component phenotype (also referred to as an endophenotype) can be a component phenotype that has a certain threshold significance/weight based on one or a plurality of factors. The relevant component phenotype can be a component phenotype having a threshold value of, for example, severity, age of onset, specificity to the trait or disease, or a combination. The relevant component phenotype can be a component phenotype associated with a network or pathway of interest. The relevant component phenotype can be a component phenotype specific to the network or pathway of interest.

The threshold value can be any useful value (relevant to the parameter involved). The threshold value can be selected based on the principles described in the disclosed model. In general, higher (more rigorous or exclusionary) thresholds can provide more significant associations. However, higher threshold values can also limit the number of elements identified as associated with a trait, thus potentially limiting the useful information generated by the disclosed methods. Thus, a balance can be sought in setting threshold values. The nature of a threshold value can depend on the factor or feature being assessed. Thus, for example, a threshold value can be a quantitative value (where, for example, the feature can be quantified) or a qualitative value, such as a particular form of the feature, for example.

The disclosed model and methods provide more accurate and broader-based identification of trait-associated elements by preferentially analyzing relevant component phenotypes and relevant elements. Such relevant component phenotypes and relevant elements have, according to the disclosed model, more significance to traits of interest, such as diseases. By using relevant component phenotypes and relevant elements, the disclosed model and methods reduce or eliminate the confounding and obscuring effect less relevant phenotypes and elements have to a given trait. This allows more, and more significant, trait associations to be identified.

The association of the relevant element with the relevant component phenotype can be identified by identifying the association of the relevant element with, for example, a network or pathway associated with the relevant component phenotype. The network or pathway can be associated with the relevant component phenotype when the relevant component phenotype occurs or is affected when the network or pathway is altered.

Additionally, the association of the relevant element with the relevant component phenotype can be identified by a threshold value of the coincidence of the relevant element and the relevant component phenotype within a set of discovery samples. Threshold value of coincidence can refer to the coincidence (that is, correlation of occurrence/presence) of the element and the component phenotype. Such a coincidence can be a basic observation of the disclosed method. The significance of this coincidence is enhanced (relative to prior methods of associating elements to diseases) by the selection of relevant elements and relevant component phenotypes, based on the plurality of factors as discussed herein.

Discovery samples can be any sample in which the presence, absence and/or level or amount of an element can be assessed. Generally, a set of discovery samples can be selected to allow assessment of the coincidence of component phenotypes with elements. For example, a set of discovery samples can be selected or identified based on principles described in the disclosed model. The set of discovery samples can comprise, for example, samples from a single individual, samples from a single pedigree, samples from a subset of a single cohort, samples from a single cohort, samples from multiple individuals, samples from multiple unrelated individuals, samples from multiple affected sib-pairs, samples from multiple pedigrees, a combination thereof, and the like. The set of discovery samples can also comprise, for example, both affected samples and unaffected samples, wherein affected samples are samples associated with the relevant component phenotype, wherein unaffected samples are samples not associated with the relevant component phenotype. Samples associated with the relevant component phenotype can be samples that exhibit, or that come from cells, tissue, or individuals that exhibit, the relevant component phenotype. Samples unassociated with the relevant component phenotype can be samples that do not exhibit, and that do not come from cells, tissue, or individuals that exhibit, the relevant component phenotype. The methods can further comprise selecting a set of discovery samples, wherein the set of discovery samples consist of samples from a single individual, samples from a single pedigree, samples from a subset of a single cohort, or samples from a single cohort. The relevant element can be selected from variant genetic elements identified in the discovery samples.

The threshold value of importance of the element to homeostasis relevant to the trait or disease can be, for example, derived from the phenotype of knock-out, transgenesis, silencing or overexpression of the element in an animal model or cell line; the phenotype of a genetic lesion in the element in a human or model inherited disorder; the phenotype of knock-out, transgenesis, silencing or overexpression of an element related to the element in an animal model or cell line; the phenotype of a genetic lesion in an element related to the element in a human or model inherited disorder; knowledge of the function of the element in a related species, a combination, and the like. The element related to the element can be a gene family member or an element with sequence similarity to the element.

The threshold value of intensity of the perturbation of the element can be, for example, derived from the type of element, the amount or level of the element, or a combination. The relevant element can be a relevant genetic element, wherein the type of element is a type of genetic variant, wherein the type of genetic element is a regulatory variant, a non-regulatory variant, a non-synonymous variant, a synonymous variant, a frameshift variant, a variant with a severity score at, above, or below a threshold value, a genetic rearrangement, a copy number variant, a gene expression difference, an alternative splice isoform, a combination, and the like. The relevant element can be a relevant genetic element, wherein the amount or level of the element is the number of copies of the relevant genetic element, the magnitude of expression of the genetic element, a combination, and the like.

The element can be an environmental condition, and the threshold value of duration of the effect of the element can be derived, for example, from the duration of an environmental condition or the duration of exposure to an environmental condition.

The element can be a genetic element, and the threshold value of duration of the effect of the element can be derived from, for example, the duration of expression of the genetic element, the expressivity of the genetic element, or a combination.

The threshold value of severity of the component phenotype can be derived, for example, from the frequency of the component phenotype, the intensity of the component phenotype, the amount of a feature of the component phenotype, or a combination.

The threshold value of specificity to the trait or disease of the component phenotype can be derived, for example, from the frequency with which the component phenotype is present in other traits or diseases, the frequency with which the component phenotype is present in the trait or disease, or a combination. For example, the component phenotype can be not present in other traits or diseases; the component phenotype can be always present in the trait or disease; the component phenotype can be not present in other traits or diseases and can always be present in the trait or disease; and the like.

The methods can further comprise selecting an element as the relevant element by assessing, for example, the value of importance of the element to homeostasis relevant to the trait or disease, intensity of the perturbation of the element, duration of the effect of the element, or a combination and comparing the value to the threshold value. One skilled in the art will recognize that comparison of the value to the threshold value can be successful if the threshold is exceeded or if the threshold is not exceeded. Success can depend upon what the value and the threshold value represents.

The methods can further comprise selecting a component phenotype as the relevant component phenotype by assessing the value of clinical features of the phenotype, and comparing the value to the threshold value. The clinical features of the phenotype can comprise, for example, the value of severity, age of onset, duration, specificity to the phenotype, response to a treatment or a combination. The methods can further comprise selecting a component phenotype as the relevant component phenotype by assessing the value of laboratory features of the phenotype, and comparing the value to the threshold value.

The variant genetic elements can be identified, for example, by sequencing nucleic acids from the discovery samples and comparing the sequences to one or more reference sequence databases. The comparison can involve, but is not limited to, BLAST alignments, megaBLAST alignments, GMAP alignments, BLAT alignments, a combination, and the like. The reference sequence database can be, but is not limited to, the RefSeq genome database, the transcriptome database, the GENBANK database, a combination thereof, and the like. The variant genetic elements identified in the discovery samples can be part of a catalog of variant genetic elements identified in a plurality of sets of discovery samples. The variant genetic elements can be filtered to select candidate variant genetic elements, wherein the variant genetic elements are filtered, for example, by selecting variant genetic elements that are present in a threshold number of sequence reads, are present in a threshold percentage of sequence reads, are represented by a threshold read quality score at variant base(s), are present in sequence reads from in a threshold number of strands, are aligned at a threshold level to a reference sequence, are aligned at a threshold level to a second reference sequence, are variants that do not have biasing features bases within a threshold number of nucleotides of the variant, a combination thereof, and the like.

The candidate variant genetic elements can be prioritized to select relevant variant genetic elements, wherein the candidate variant genetic elements are prioritized, for example, according to the presence in the candidate variant genetic element of a non-synonymous variant in a coding region, the presence of the candidate variant genetic element in a plurality of samples, the presence of the candidate variant genetic element at a chromosomal location having a quantitative trait locus associated with the trait or disease, the severity of the putative functional consequence that the candidate variant genetic element represents, association of the candidate variant genetic element with a network or pathway in a plurality of samples, association of the candidate variant genetic element with a network or pathway with which one or more other candidate variant genetic elements are associated, the plausibility or presence of a functional relationship between the candidate variant genetic element and the relevant component phenotype, a combination thereof, and the like.

The association of a relevant element with a relevant component phenotype of the trait or disease can be performed, for example, for a plurality of relevant elements, a plurality of relevant component phenotypes of the trait or disease, or a plurality of relevant elements and a plurality of relevant component phenotypes of the trait or disease.

The methods can further comprise validating the association of the relevant element with the relevant component phenotype. Association of the relevant element with the relevant component phenotype can be validated by assessing the association of the relevant element with the relevant component phenotype in one or more sets of validation samples, wherein the set of validation samples is different than the samples from which the relevant element was selected. The set of validation samples can comprise samples from a single individual, samples from a single pedigree, samples from a subset of a single cohort, samples from a single cohort, samples from multiple individuals, samples from multiple unrelated individuals, samples from multiple affected sib-pairs, samples from multiple pedigrees, a combination, and the like.

Although the disclosed model and methods include the use of new traits, phenotypes, elements and the like, the disclosed model and methods also represent a new use of the many traits, phenotypes, elements and the like that are known and used in genetic and disease analysis. The disclosed model and methods use these traits, phenotypes, elements and the like in selective and weighted ways as describe herein. Those of skill in the art are aware of many traits, phenotypes, elements and the like as well as methods and techniques of their detection, measurement, assessment. Such traits, phenotypes, elements, methods and techniques can be used with the disclosed model and methods based on the principles and description herein and such use is specifically contemplated.

III. Exemplary Systems

Figure 4:
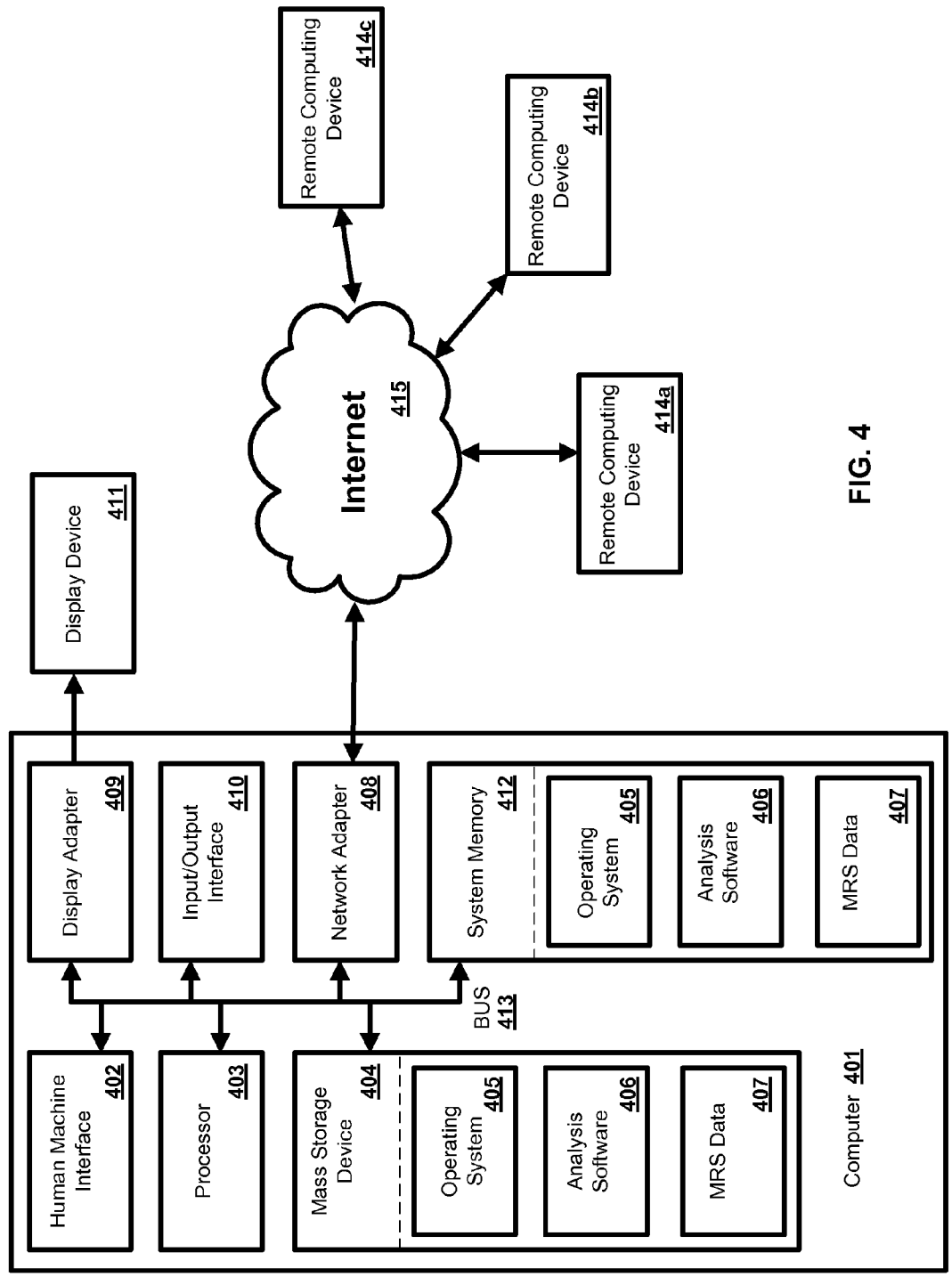
FIG. 4 is a block diagram illustrating an exemplary operating environment for performing the disclosed method.

FIG. 4 is a block diagram illustrating an exemplary operating environment for performing the disclosed method. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment. One skilled in the art will appreciate that this is a functional description and that the respective functions can be performed by software, hardware, or a combination of software and hardware.

The present methods and systems can be operational with numerous other general purpose or special purpose computing system environments or configurations. Examples of well known computing systems, environments, and/or configurations that can be suitable for use with the system and method comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

Further, one skilled in the art will appreciate that the systems and methods disclosed herein can be implemented via a general-purpose computing device in the form of a computer 401. The components of the computer 401 can comprise, but are not limited to, one or more processors or processing units 403, a system memory 412, and a system bus 413 that couples various system components including the processor 403 to the system memory 412.

The system bus 413 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (USA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI) bus also known as a Mezzanine bus. The bus 413, and all buses specified in this description can also be implemented over a wired or wireless network connection and each of the subsystems, including the processor 403, a mass storage device 404, an operating system 405, analysis software 406, MRS data 407, a network adapter 408, system memory 412, an Input/Output Interface 410, a display adapter 409, a display device 411, and a human machine interface 402, can be contained within one or more remote computing devices 414a,b,c at physically separate locations, connected through buses of this form, in effect implementing a fully distributed system.

The computer 401 typically comprises a variety of computer readable media. Exemplary readable media can be any available media that is accessible by the computer 401 and comprises, for example and not meant to be limiting, both volatile and non-volatile media, removable and non-removable media. The system memory 412 comprises computer readable media in the form of volatile memory, such as random access memory (RAM), and/or non-volatile memory, such as read only memory (ROM). The system memory 412 typically contains data such as MRS data 407 and/or program modules such as operating system 405 and analysis software 406 that are immediately accessible to and/or are presently operated on by the processing unit 403.

In another aspect, the computer 401 can also comprise other removable/non-removable, volatile/non-volatile computer storage media. By way of example, FIG. 4 illustrates a mass storage device 404 which can provide non-volatile storage of computer code, computer readable instructions, data structures, program modules, and other data for the computer 401. For example and not meant to be limiting, a mass storage device 404 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 404, including by way of example, an operating system 405 and analysis software 406. Each of the operating system 405 and analysis software 406 (or some combination thereof) can comprise elements of the programming and the analysis software 406. MRS data 407 can also be stored on the mass storage device 404. MRS data 407 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 401 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 403 via a human machine interface 402 that is coupled to the system bus 413, but can be connected by other interface and bus structures, such as a parallel port, game port, an IEEE 1394 Port (also known as a Firewire port), a serial port, or a universal serial bus (USB).

In yet another aspect, a display device 411 can also be connected to the system bus 413 via an interface, such as a display adapter 409. It is contemplated that the computer 401 can have more than one display adapter 409 and the computer 401 can have more than one display device 411. For example, a display device can be a monitor, an LCD (Liquid Crystal Display), or a projector. In addition to the display device 411, other output peripheral devices can comprise components such as speakers (not shown) and a printer (not shown) which can be connected to the computer 401 via Input/Output Interface 410. Any step and/or result of the methods disclosed can be output in any form known in the art to any output device (such as a display, printer, speakers, etc.) known in the art.

The computer 401 can operate in a networked environment using logical connections to one or more remote computing devices 414*a,b,c*. By way of example, a remote computing device can be a personal computer, portable computer, a server, a router, a network computer, a peer device or other common network node, and so on. Logical connections between the computer 401 and a remote computing device 414*a,b,c* can be made via a local area network (LAN) and a general wide area network (WAN). Such network connections can be through a network adapter 408. A network adapter 408 can be implemented in both wired and wireless environments. Such networking environments are conventional and commonplace in offices, enterprise-wide computer networks, intranets, and the Internet 415.

The processing of the disclosed methods and systems can be performed by software components. The disclosed system and method can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed method can also be practiced in grid-based and distributed computing environments where tasks are performed by remote processing devices that are linked through a communications network. In a distributed computing environment, program modules can be located in both local and remote computer storage media including memory storage devices.

In one aspect, the methods can be implemented in a software system that can utilize data management services, an analysis pipeline, and internet-accessible software for variant discovery and analysis for ultra-high throughput, next generation medical resequencing (MRS) data with minimal human manipulation. The software system cyberinfrastructure can use an n-tiered architecture design, with a relational database, middleware and a web server. The data management services can include organizing reads into a searchable database, secure access and backups, and data dissemination to communities over the internet The automatic analysis pipeline can be based on pair-wise megaBLAST or GMAP alignments and an Enumeration and Characterization module designed for identification and characterization of variants. The variant pipeline can be agnostic as to the read type or the sequence library searched, including RefSeq genome and transcriptome databases.

Data, analysis and results can be delivered to the community using an application server provider implementation, eliminating the need for client-side support of the software. Dynamic queries and visualization of read data, variant data and results can be provided with a user interface. The software system can report, for example, sSNPs, nsSNPs, indels, premature stop codons, and splice isoforms. Read coverage statistics can be reported by gene or transcript, together with a visualization module based upon an individual transcript or genomic segment. As needed, data access can be restricted using security procedures including password protection and HTTPS protocols.

In an aspect, reads can be received in, for example, FASTA format with associated quality score numbers. For example, 454 quality scores can be supplied in "pseudo phred" format (FASTA format with space delimited base 10 ASCII representations of integers in lieu of base pairs). The FASTA headers contain metadata for the sequence including an identifier and sample-specific information. The concept of a sample can be equivalent to an individual run or a specific sample. Data inputs (sequences, lengths and quality scores) can automatically be parsed and loaded into a single relational database table linked to a representation of the sample.

In one aspect, the software system can generate alignments to the NCBI human genome and RefSeq transcript libraries, which includes both experimentally-verified (NM and NR accessions) and computationally predicted transcripts (XM and XR accessions). Reference sequence data, location based feature information (e.g. CDS annotations, variation records) and basic feature metadata imported and stored in an application specific schema.

In a further aspect, reads and quality data can be imported and aligned pairwise to sequence libraries using, for example, MegaBLAST or GMAP. MegaBLAST alignment parameters can be adapted from those used to map SNPs to the human genome: wordsize can be 14; identity count can be >35; expect value filter can be e-10; and low-complexity sequence can not be allowed to seed alignments, but alignments can be allowed to extend through such regions. GMAP parameters can be: identity count can be >35 and identity can be >95%. The best-match alignments for reads can be imported into the database. All alignments equivalent in quality to the best match can be accepted (as in the case of hits to shared exons in splice variants).

All positions at which a read differs from the aligned reference sequence can be enumerated. Contiguous indel events can be treated as single polymorphisms. All occurrences of potential polymorphisms in reads with respect to a given position can be unified as a "single polymorphism," with associated statistics on frequency, alignment quality, base quality, and other attributes that may be used to assess the likelihood that the polymorphism is a true variant. Candidate variants can be further characterized by type (SNP, indel, splice isoform, stop codon) and as synonymous variant (sV) or non-synonymous variant (nsV).

Figure 5:
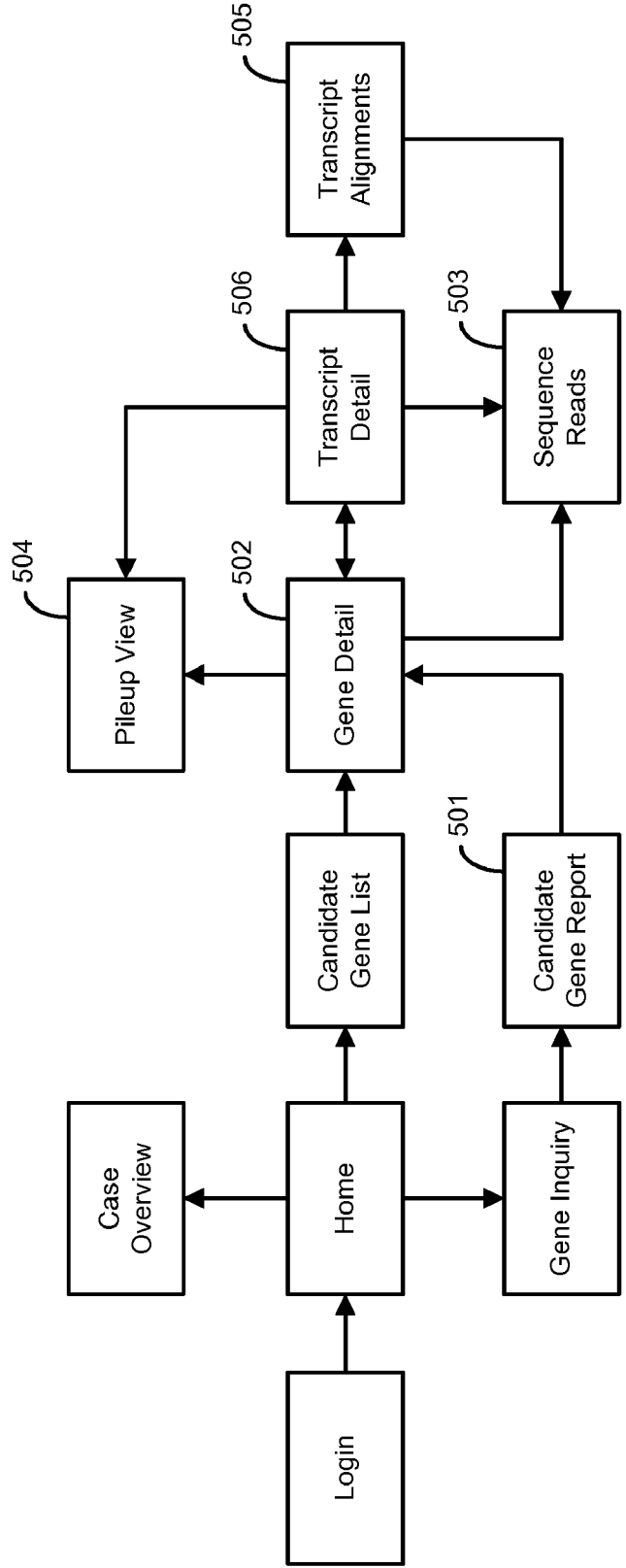
FIG. 5 is a block diagram illustrating an exemplary web-based navigation map. Several user-driven query and reporting functions can be implemented.

A web-based, user interface can be used to allow data navigation and viewing using a wide variety of paths and filters. FIG. 5 illustrates an exemplary web-based navigation map. Several user-driven query and reporting functions can be implemented. Users can search based upon a gene name or symbol and view their associated reads. Users can also search based upon all genes that meet selectable read coverage, variant frequency, or variant type criteria. FIG. 6 provides an exemplary sequence query interface. Alternatively, a list of candidate genes, supplied prospectively, can be used as an entry point into the results. Resultant data can be further filtered by case, sample or associated read count. Users can search a sample or set of samples. Users can specify the alignment algorithm and reference database from drop down lists. The result of the query can be a sortable Candidate Gene Report 501 table that features, for example, gene symbol (linked to Gene Detail 502 page), gene description, the transcripts or genome segments associated with the gene, sequencing read count total for all matches, and chromosome location. List results can be exportable to Excel and in XML and PDF formats.

Once a gene of interest has been selected, the user can have access to a detailed gene information page. This page can present gene-centric information, for example, synonyms, chromosome position and links to cytogenetic maps, disease association and transcript details at NCBI. For each gene, the gene information page can also display the associated transcripts, genomic segments, reads and variants grouped by case or sample. Links can be made available to views of Sequence Reads 503 and the Pileup View 504. The Sequence Reads 503 page can present a textual display of all annotated reads (with read identifier, length and average quality score) by case number along with the transcript name to which they map (linked to Alignments 505). In Alignments 505, each nucleotide in the read can be color coded with the base quality score to enable facile scanning of overall and position-specific read quality.

The Details 506 page can present a tabular view of all gene segment or transcript associated Sequence Reads 503, pair wise Alignments 505 and a comprehensive read overview (Pileup View 504) grouped by case or sample. It can also provide a table of all variants in cases grouped into SNP, indel and splice variant. For each identified variant, there can be drill-down links to relevant Sequence Reads 503 and pair wise BLAST- or GMAP-generated Alignments 505.

Figure 7A:
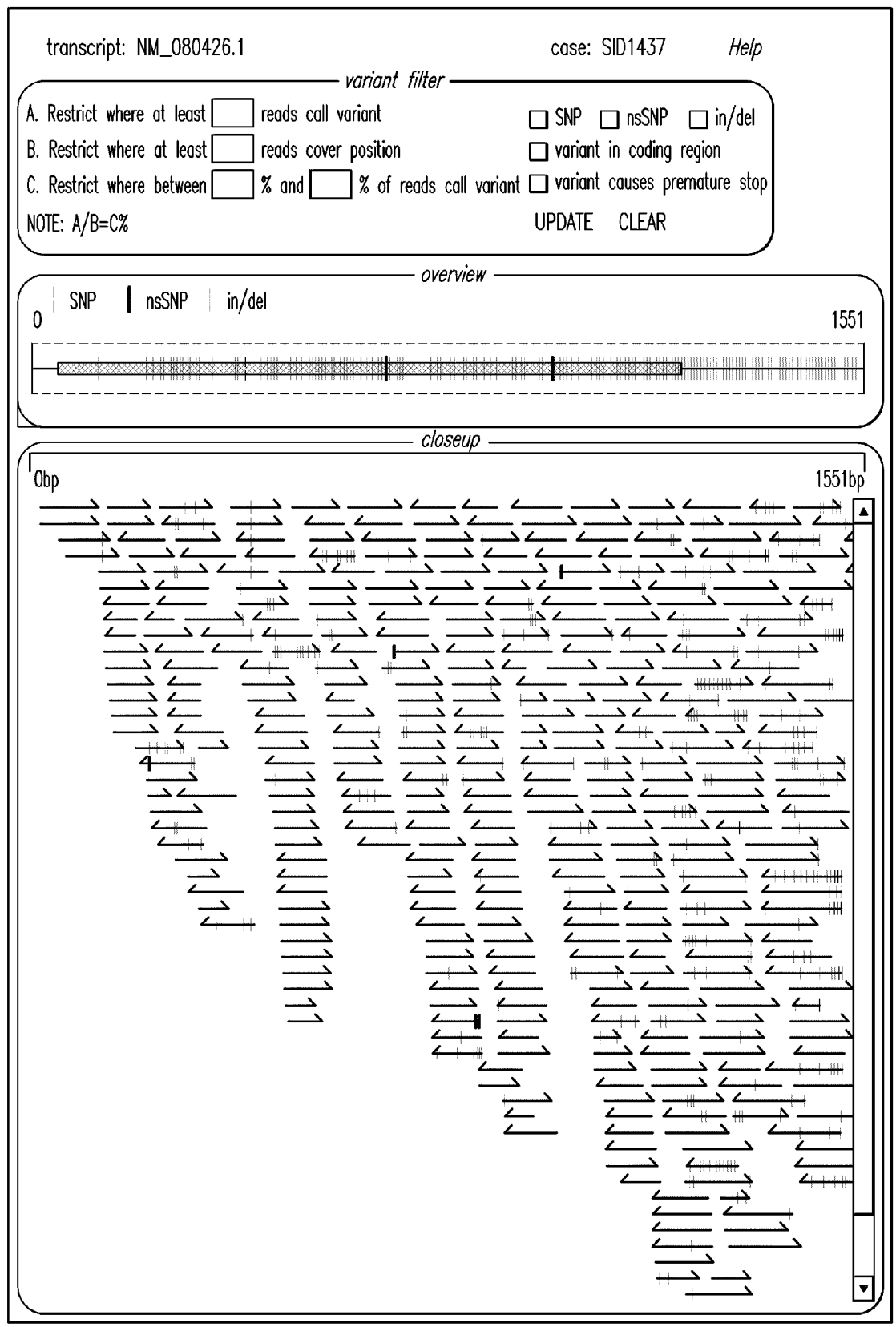
FIG. 7A displays all putative variants.
Figure 7B:
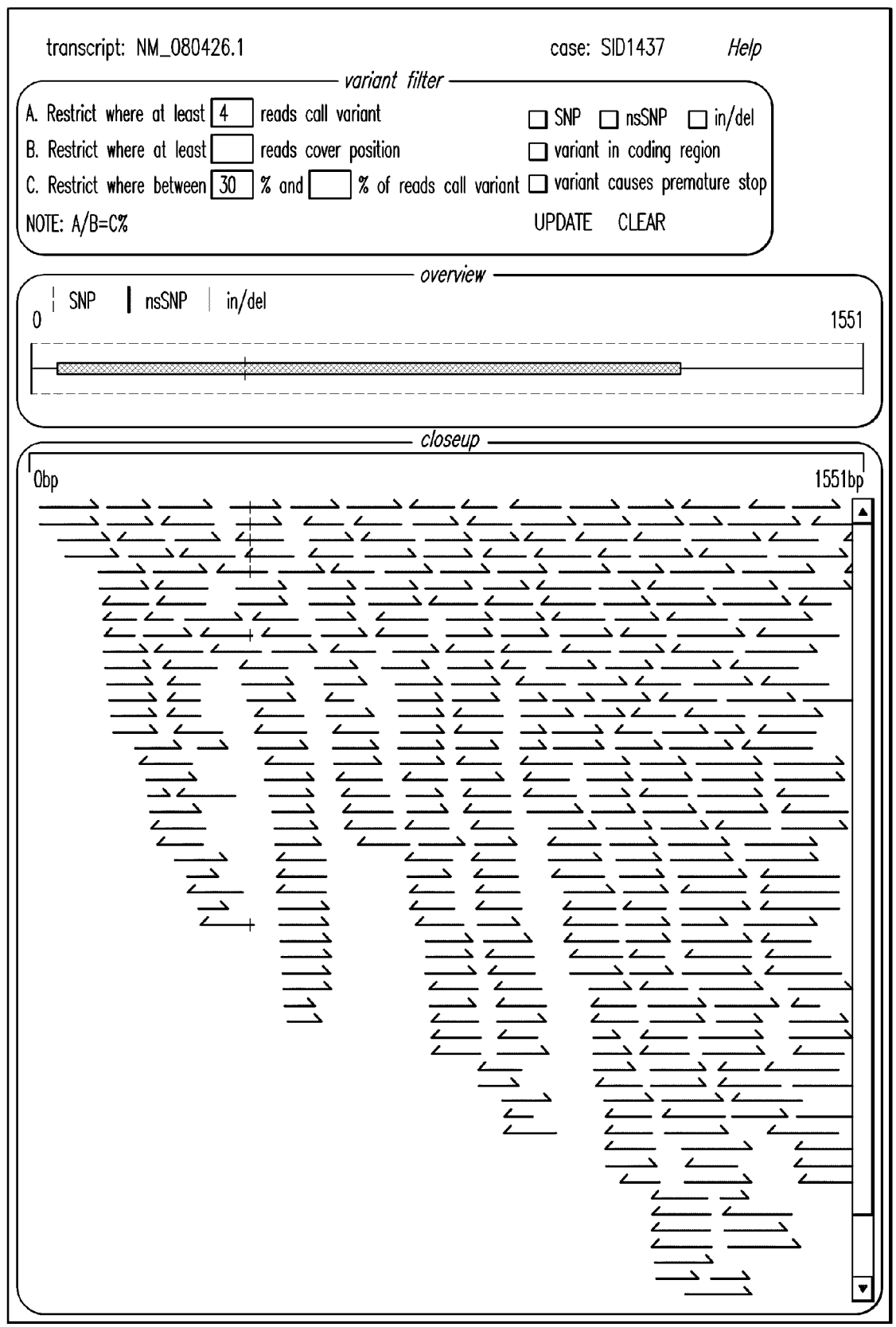
FIG. 7B displays variants filtered to retain those present in =4 reads, in 30% of reads aligned at that position, and in bidirectional reads.

The Pileup View 504 is further illustrated in FIG. 7. The Pileup View 504 can display reads from a single sample aligned against a transcript or genomic segment, along with all nucleotide variants detected in those reads. FIG. 7 illustrates the identification of a coding domain (CD) SNP in the α subunit of the Guanine nucleotide-binding stimulatory protein (GNAS) using the disclosed methods. GNAS is a schizophrenia candidate gene, with a complex imprinted expression pattern, giving rise to maternally, paternally, and biallelically expressed transcripts that are derived from four alternative promoters and 5' exons. The 1884 bp GNAS transcript, NM_080426.1, is indicated by a horizontal line, oriented from 5' to 3', from left to right), along with its associated CD (in green). Three hundred and ninety four 454 reads from sample 1437 are displayed as arrows aligned against NM_080426.1 whose direction reflects their orientation with respect to the transcript. Variants found in individual reads are displayed by hash marks at their relative position on the read. Variants are characterized as synonymous SNPs (sSNPs, blue), nsSNPs (red) and deletions or insertions (black) with respect to individual sequence read alignments. The left panel displays all putative variants (FIG. 7A). The right panel displays variants filtered to retain those present in =4 reads, in 30% of reads aligned at that position, and in bidirectional reads (FIG. 7B). One sSNP (C398T) was retained that was present in seven of thirteen reads aligned at that position in sample 1437, nine of eighteen reads in sample 1438 and twenty of twenty-one reads in 1439. C398T is validated (dbSNP number rs7121), and the homozygous 398T allele has shown association with deficit schizophrenia.

In one aspect, the analysis software 406 can implement any of the methods disclosed. For example, the analysis software 406 can implement a method for determining a candidate biological molecule variant comprising receiving biological molecule sequence data, annotating the biological molecule sequence data wherein the step of annotating results in identification of a plurality of biological molecules, determining if the at least one of the plurality of biological molecules is a potential biological molecule variant of a known biological molecule, filtering the biological molecule sequence data to determine if the determined potential biological molecule variant is a candidate biological molecule variant, prioritizing the candidate biological molecule variants, and presenting a list of the plurality of the candidate biological molecule variants.

In another aspect, the analysis software 406 can implement a method for determining an association between a biological molecule variant and a component phenotype comprising receiving biological molecule sequence data comprising a plurality of biological molecule variants, determining a homeostatic effect for at least one of the plurality of biological molecule variants, determining an intensity of perturbation for the at least one of the plurality of biological molecule variants, determining a duration of effect for the at least one of the plurality of biological molecule variants, compiling the at least one of the plurality of biological molecule variants into at least one biological pathway based on the homeostatic effect, the intensity of perturbation, and the duration of effect, determining if the at least one biological pathway is associated with the component phenotype, and presenting a list comprising the plurality of biological molecule variants in the at least one biological pathway associated with the component phenotype.

For purposes of illustration, application programs and other executable program components such as the operating system 405 are illustrated herein as discrete blocks, although it is recognized that such programs and components reside at various times in different storage components of the computing device 401, and are executed by the data processor(s) of the computer. An implementation of analysis software 406 can be stored on or transmitted across some form of computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any method or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

IV. Schizophrenia-Associated Genes

Schizophrenia and Bipolar Affective Disorder are common and debilitating psychiatric disorders. Despite a wealth of information on the epidemiology, neuroanatomy and pharmacology of the illness, it is uncertain what molecular pathways are involved and how impairments in these affect brain development and neuronal function. Despite an estimated heritability of 60-80%, very little is known about the number or identity of genes involved in these psychoses. Although there has been recent progress in linkage and association studies, especially from genome-wide scans, these studies have yet to progress from the identification of susceptibility loci or candidate genes to the full characterisation of disease-causing genes (Berrettini, 2000).

Disclosed are the GPX, GSPT1 and TKT genes, polynucleotide fragments comprising one or more of GPX, GSPT1 and TKT genes or a fragment, derivative or homologue thereof, the gene products of the GPX, GSPT1 and TKT genes, polypeptide fragments comprising one or more of the gene product of the GPX, GSPT1 and TKT genes or a fragment, derivative or homologue thereof. It has been discovered that genetic variations in the GPX, GSPT1 and TKT genes are associated with schizophrenia.

Also disclosed is a recombinant or synthetic polypeptide for the manufacture of reagents for use as therapeutic agents in the treatment of schizophrenia and/or affective psychosis. In particular, disclosed are pharmaceutical compositions comprising the recombinant or synthetic polypeptide together with a pharmaceutically acceptable carrier therefor.

Also disclosed is a method of diagnosing schizophrenia and/or affective psychosis or susceptibility to schizophrenia and/or affective psychosis in an individual or subject, wherein the method comprises determining if one or more of the GPX, GSPT1 and TKT genes in the individual or subject contains a genetic variation. The genetic variation can be a genetic variation identified as associated with schizophrenia, affective psychosis disorder or both.

The methods which can be employed to detect genetic variations are well known to those of skill in the art and could be detected for example using PCR or in hybridization studies using suitable probes which could be designed to span an identified mutation site in one or more of the GPX, GSPT1 and TKT genes, such as the mutations described herein.

Once a particular polymorphism or mutation has been identified it is possible to determine a particular course of treatment. For example the GPX, GSPT1 and TKT genes are implicated in brain glutathione levels. Thus, treatments to change brain glutathione levels are contemplated for individuals or subjects determined to have a genetic variation in one or more of the GPX, GSPT1 and TKT genes.

It will be appreciated that mutations in the gene sequence or controlling elements of a gene, eg. a promoter and/or enhance can have subtle effects such as affecting mRNA splicing/stability/activity and/or control of gene expression levels, which can also be determined. Also the relative levels of RNA can be determined using for example hybridization or quantitative PCR as a means to determine if the one or more of the GPX, GSPT1 and TKT genes has been mutated or disrupted.

Moreover the presence and/or levels of one or more of the GPX, GSPT1 and TKT gene products themselves can be assayed by immunological techniques such as radioimmunoassay, Western blotting and ELISA using specific antibodies raised against the gene products. Also disclosed are antibodies specific for one or more of the GPX, GSPT1 and TKT gene products and uses thereof in diagnosis and/or therapy.

Also disclosed are antibodies specific to the disclosed GPX, GSPT1 and TKT polypeptides or epitopes thereof. Production and purification of antibodies specific to an antigen is a matter of ordinary skill, and the methods to be used are clear to those skilled in the art. The term antibodies can include, but is not limited to polyclonal antibodies, monoclonal antibodies (mAbs), humanised or chimeric antibodies, single chain antibodies, Fab fragments, F(ab')$_2$ fragments, fragments produced by a Fab expression library, anti-idiotypic (anti-Id) antibodies, and epitope binding fragments of any of the above. Such antibodies can be used in modulating the expression or activity of the particular polypeptide, or in detecting said polypeptide in vivo or in vitro.

Using the sequences disclosed herein, it is possible to identify related sequences in other animals, such as mammals, with the intention of providing an animal model for psychiatric disorders associated with the improper functioning of the disclosed nucleotide sequences and proteins. Once identified, the homologous sequences can be manipulated in several ways known to the skilled person in order to alter the functionality of the nucleotide sequences and proteins homologous to the disclosed nucleotide sequences and proteins. For example, "knock-out" animals can be created, that is, the expression of the genes comprising the nucleotide sequences homologous to the disclosed nucleotide sequences and proteins can be reduced or substantially eliminated in order to determine the effects of reducing or substantially eliminating the expression of such genes. Alternatively, animals can be created where the expression of the nucleotide sequences and proteins homologous to the disclosed nucleotide sequences and proteins are upregulated, that is, the expression of the genes comprising the nucleotide sequences homologous to the disclosed nucleotide sequences and proteins can be increased in order to determine the effects of increasing the expression of these genes. In addition to these manipulations substitutions, deletions and additions can be made to the nucleotide sequences encoding the proteins homologous to the disclosed nucleotide sequences and proteins in order to effect changes in the activity of the proteins to help elucidate the function of domains, amino acids, etc. in the proteins. Furthermore, the disclosed sequences can also be used to transform animals to the manner described above. The manipulations described above can also be used to create an animal model of schizophrenia and/or affective psychosis associated with the improper functioning of the disclosed nucleotide sequences and/or proteins in order to evaluate potential agents which can be effective for combating psychotic disorders, such as schizophrenia and/or affective psychosis.

Thus, also disclosed are screens for identifying agents suitable for preventing and/or treating schizophrenia and/or affective psychosis associated with disruption or alteration in the expression of one or more of the GPX, GSPT1 and TKT genes and/or its gene products. Such screens can easily be adapted to be used for the high throughput screening of libraries of compounds such as synthetic, natural or combinatorial compound libraries.

Thus, one or more of the GPX, GSPT1 and TKT gene products can be used for the in vivo or in vitro identification of novel ligands or analogs thereof. For this purpose binding studies can be performed with cells transformed with the disclosed nucleotide fragments or an expression vector comprising a disclosed polynucleotide fragment, said cells expressing one or more of the GPX, GSPT1 and TKT gene products.

Alternatively also one or more of the GPX, GSPT1 and TKT gene products as well as ligand-binding domains thereof can be used in an assay for the identification of functional ligands or analogs for one or more of the GPX, GSPT1 and TKT gene products.

Methods to determine binding to expressed gene products as well as in vitro and in vivo assays to determine biological activity of gene products are well known. In general, expressed gene product is contacted with the compound to be tested and binding, stimulation or inhibition of a functional response is measured.

Thus, also disclosed is a method for identifying ligands for one or more of the GPX, GSPT1 and TKT gene products, said method comprising the steps of:

(a) introducing into a suitable host cell a polynucleotide fragment one or more of the GPX, GSPT1 and TKT gene products;
(b) culturing cells under conditions to allow expression of the polynucleotide fragment;
(c) optionally isolating the expression product;
(d) bringing the expression product (or the host cell from step b)) into contact with potential ligands which will possibly bind to the protein encoded by said polynucleotide fragment from step a);
(e) establishing whether a ligand has bound to the expressed protein; and
(f) optionally isolating and identifying the ligand.
As a preferred way of detecting the binding of the ligand to the expressed protein, also signal transduction capacity can be measured.

Compounds which activate or inhibit the function of one or more of the GPX, GSPT1 and TKT gene products can be employed in therapeutic treatments to activate or inhibit the disclosed polypeptides.

Schizophrenia and/or affective psychosis as used herein relates to schizophrenia, as well as other affective psychoses such as those listed in "The ICD -10 Classification of Mental and Behavioural Disorders" World Health Organization, Geneva 1992. Categories F20 to F29 inclusive includes Schizophrenia, schizotypal and delusional disorders. Categories F30 to F39 inclusive are Mood (affective) disorders that include bipolar affective disorder and depressive disorder. Mental Retardation is coded F70 to F79 inclusive. The Diagnostic and Statistical Manual of Mental Disorders, Fourth Edition (DSM-IV). American Psychiatric Association, Washington D.C. 1994.

"Polynucleotide fragment" as used herein refers to a chain of nucleotides such as deoxyribose nucleic acid (DNA) and transcription products thereof, such as RNA. The polynucleotide fragment can be isolated in the sense that it is substantially free of biological material with which the whole genome is normally associated in vivo. The isolated polynucleotide fragment can be cloned to provide a recombinant molecule comprising the polynucleotide fragment. Thus, "polynucleotide fragment includes double and single stranded DNA, RNA and polynucleotide sequences derived therefrom, for example, subsequences of said fragment and which are of any desirable length. Where a nucleic acid is single stranded then both a given strand and a sequence or reverse complementary thereto is contemplated.

In general, the term "expression product" or "gene product" refers to both transcription and translation products of said polynucleotide fragments. When the expression or gene product is a "polypeptide" (i.e. a chain or sequence of amino acids displaying a biological activity substantially similar (eg. 98%, 95%, 90%, 80%, 75% activity) to the biological activity of the protein), it does not refer to a specific length of the product as such. Thus, it should be appreciated that "polypeptide" encompasses inter alia peptides, polypeptides and proteins. The polypeptide can be modified in vivo and in vitro, for example by glycosylation, amidation, carboxylation, phosphorylation and/or post-translational cleavage.

V. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Mendelian Disorders

The disclosed model notes that:

$$g(E_{1\ldots n})=h(Cp_{1\ldots n}, Sv_{1\ldots n}, A_{1\ldots n})$$

For Mendelian disorders, there is typically a single value for E (the causal gene), H (the impact of the causal gene on relevant homeostasis), t (the time at which the causal gene is expressed) and Cp (a pathognomonic phenotype).

Thus:

$$g(E_1)=h(Cp_1, Sv_{1\ldots n}, A_{1\ldots n})$$

Therefore, for a Mendelian disorder in an individual patient, variation in the value of I (the specific variant in the causal gene) determines the value of Sv (phenotype severity) and A (age of onset). This is in agreement with most evidence in Mendelian disorders. For example, the magnitude of triplet repeat expansions generally is associated with severity and age of onset of symptoms.

B. Hypertension

Multiple, rare families that exhibited Mendelian segregation of the phenotype (Cp) of severe hypertension were studied to identify single gene mutations (E) that result in a phenotype indistinguishable from that of a common, complex disorder—namely hypertension. The majority of the individual genes that had mutations (E) and resulted in the hypertension phenotype could be collapsed into a single metabolic pathway (P). Thus, these studies agree with the model described herein, namely the convergence of distinct Elements (E) Into Networks and Pathways (P) in causality of common, complex disorders.

C. Cancer

Recently, researchers undertook medical sequencing of 13,023 genes in 11 breast and 11 colorectal cancers. The study revealed that individual tumors accumulate an average of ~90 mutant genes but that only α subset of these contribute to the neoplastic process. Using criteria to delineate this subset, the researchers identified 189 genes (11 per tumor) that were mutated at significant frequency. The majority of these genes were not known to be genetically altered in tumors and were predicted to affect a wide range of cellular functions, including transcription, adhesion, and invasion. This study agrees with the model described herein, namely that in complex diseases, there is insufficient homogeneity of causal elements among affected individuals to enable detection of statistical differences. The disclosed model notes that there exists significant genetic and environmental heterogeneity in complex diseases. Thus the specific combinations of genetic and environmental elements that cause D vary widely among the affected individuals in a cohort. In agreement with this study, experimental designs based upon comparisons of candidate variant allele frequencies between affected and unaffected cohorts, even if undertaken on a large scale, will fail to disclose causal variants in situations where there is a high degree of heterogeneity among individuals in causal elements.

Another study showed similar findings. Comprehensive, shotgun sequencing of tumor transcriptomes of surgical specimens from individual mesothelioma tumors, an environmentally-induced cancer, was performed. High-throughput pyrosequencing was used to generate 1.6 gigabases of transcriptome sequence from enriched tumor specimens of four mesotheliomas (MPM) and two controls. A bioinformatic pipeline was used to identify candidate causal mutations, namely non-synonymous variants (nsSNPs), in tumor-expressed genes. Of ~15,000 annotated (RefSeq) genes evaluated in each specimen, 66 genes with previously undescribed nsSNPs were identified in MPM tumors. Genomic resequencing of 19 of these nsSNPs revealed 15 to be germline variants and 4 to represent loss of heterozygosity (LOH) in MPM. Resequencing of these 4 genes in 49 additional MPM surgical specimens identified one gene (MPM1), that exhibited LOH in a second MPM tumor. No overlap was observed in other genes with nsSNPs or LOH among MPM tumors. This study agrees with the model described herein, namely that in complex diseases, there is insufficient homogeneity of causal elements among affected individuals to enable detection of statistical differences.

D. Schizophrenia
  i. Example 1

Medical sequencing was performed on three related individuals with schizophrenia, multiple expressed genes were identified with variants in each affected individual. Schizophrenia is a "complex" disorder in which inherited elements are believed to be a significant factor. Previous studies have identified some inherited elements but the most common, important contributors remain unknown. The disparate genes (E) identified in affected individuals were found to converge into several discrete pathways (P) that are disordered in schizophrenia. For example, in the affected proband, a male Caucasian of Jewish ethnicity, 621341 sequence reads were identified that matched to 15530 genes, non-synonymous single nucleotide polymorphisms in the genes glutathione peroxidase 1 (GPX1) and glutathione S-transferase pi (GSTP1). These amino-acid changes were also identified in the other two, related individuals with schizophrenia. Thus, some non-synonymous variants in patients with schizophrenia converge into the glutathione metabolism pathway.

These studies of schizophrenia also exemplified the concept of Cp, and especially molecular Cp that are suggested by the E identified in affected individuals, being informative. For example, glutathione (GSH) is converted to oxidized glutathione (GSSG) through glutathione peroxidase (GPx), and converted back to GSH by glutathione reductase (GR). Measurements of GSH, GSSG, GPx and GR in the caudate region of postmortem brains from schizophrenic patients and control subjects (with and without other psychiatric disorders) represent molecular Cp that would be of benefit to seek associations with variants in GPX1 and GSTP1 candidate genes. For example, significantly lower levels of GSH, GPx, and GR were found in schizophrenic group than in control groups without any psychiatric disorders. Concomitantly, a decreased GSH:GSSG ratio was also found in schizophrenic group. Moreover, both GSSG and GR levels were significantly and inversely correlated to age of schizophrenic patients, but not control subjects.

i. Example 2

Three lymphoblastoid, two lung and four lung cancer RNA samples were sequenced with 454 technology. The disclosed methods were used to comprehensively catalog nsV. 350 µg of total RNA was isolated from Epstein-Barr-virus-transformed lymphoblastoid cell lines from a schizophrenia pedigree (from the NIGMS Cell Repository panel, Coriell Institute for Medical Research, Camden, N.J.) and 6 lung surgical specimens. The proband had schizophrenia with primarily negative clinical features (Table 1). H is father had major depression. H is sister had anorexia nervosa and schizoid personality disorder. The mother (not studied) was not affected.

TABLE 1

Family 176 B Lymphoblastoid Cell Line Characteristics

| | Sample 1437 | Sample 1438 | Sample 1439 |
|---|---|---|---|
| Repository # | GM01488 | GM01489 | GM01490 |
| db SNP number | 10411 | 10412 | 10413 |
| Age | 23 YR | 55 YR | 27 YR |
| Gender | Male | Male | Female |
| Race | Caucasian | Caucasian | Caucasian |
| Ethnicity | Jewish | Jewish | Jewish |
| Relation | Proband | affected father | affected sister |
| Symptoms, History | paralogical thinking; affective shielding; splitting of affect from content; suspiciousness; onset age 15; hospitalized | 3 episodes of depression; ECT; no hypomania | anorexia nervosa since adolescence; more schizoid than depressed |
| ISCN | 46, XY | n.d. | n.d. |
| HLA type | Aw26, B16/Aw26, B16 | Aw26, B16/A18, B- | Aw26, B16/A2, B35 |

Figure 8:
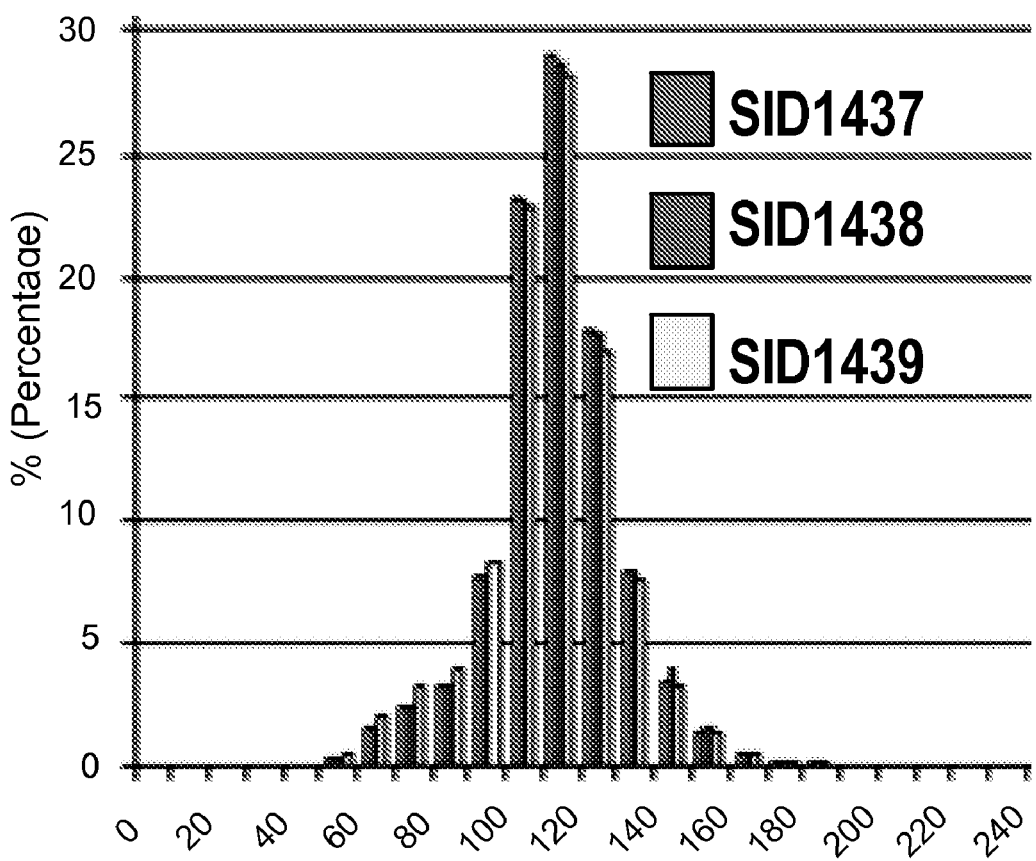
FIG. 8 is a graph showing the length distribution of 454 GS20 reads.

Poly-A+ RNA was prepared using oligo(dT) magnetic beads (PureBiotech, Middlesex, N.J.), and 1st-strand cDNA prepared from 5-8 µg of poly(A)+ RNA with 200 pmol oligo (dT) 25V (V=A, C or G) using 300 U of Superscript II reverse transcriptase (Invitrogen). Second-strand synthesis was performed at 16° C. for 2 h after addition of 10 U of E. coli DNA ligase, 40 U of E. coli DNA polymerase, and 2 U of RNase H (all from Invitrogen). T4 DNA polymerase (5 U) was added and incubated for 5 min at 16° C. cDNA was purified on QIAquick Spin Columns (Qiagen, Valencia, Calif.). Single-stranded template DNA (sstDNA) libraries were prepared using the GS20 DNA Library Preparation Kit (Roche Applied Science, Indianapolis, Ind.) following the manufacturer's recommendations. sstDNA libraries were clonally amplified in a bead-immobilized form using the GS20 emPCR kit (Roche Applied Science). sstDNA libraries were sequenced on the 454 GS20 instrument. Two runs were performed on SID1437 and SID1438, 3 runs on SID1439 (56-64 MB sequence; Table 2, FIG. 8), and up to 18 runs on each of the lung specimens (1.65 GB). FIG. 8 illustrates length distribution of 454 GS20 reads.

TABLE 2

454 GS20 Statistics

| | SID1437 | SID1438 | SID1439 |
|---|---|---|---|
| Number of GS20 runs | 2 | 2 | 3 |
| Average read length | 104 | 104 | 103 |
| Average read quality | 25 | 24 | 25 |
| Number Of Reads | 621,341 | 536,463 | 586,232 |
| Number Of Bases | 64.9 M | 56.2 M | 60.4 M |

Four alignment techniques (MegaBLAST, GMAP, BLAT and SynaSearch) were evaluated for alignment of 454 reads from SID1437 to the NCBI human genome and RefSeq transcript databases using similar parameters. MegaBLAST and BLAT are standard methods for aligning sequences that differ slightly as a result of sequencing errors. GMAP is a recently described algorithm that was developed to align cDNA sequences to a genome in the presence of substantial polymorphisms and sequence errors, and without using probabilistic splice site models. GMAP features a minimal sampling strategy for genomic mapping, oligomer chaining for approximate alignment, sandwich DP for splice site detection, and microexon identification. These features are particularly useful for alignments of short reads with relatively high base calling error rates. GMAP was also anticipated to be useful in identifying novel splice variants. Synasearch (Synamatix, Kuala Lumpur, Malaysia) is a novel, rapid alignment method.

Computationally, SynaSearch and MegaBLAST were most efficient in transcript alignments, whereas SynaSearch and GMAP had the best efficiency for genome alignments (Tables 3, 4). SynaSearch alignments were performed on a dual Itanium server while the other methods employed a much larger blade cluster. Genome alignments were much more computationally intensive than transcript alignments. GMAP aligned the greatest number of reads (82% to the human transcript database and 97.8% to the genome). The greater number of alignments to the genome reflects RefSeq having only 40,545 of ~185,000 human transcripts. For transcripts with aligned reads, GMAP provided the greatest length and depth of coverage of the methods evaluated. MegaBLAST and Synamatix performed similarly for these latter metrics, while BLAT was inferior. These comparisons indicated GMAP to be the most effective method for alignment of 454 reads to the human genome and transcript databases, and that the blade cluster was adequate for pipelining ~1 M reads per day.

TABLE 3

Comparison of alignment methods for mapping 621,341 454 reads from SID 1437

| | BLAT | GMAP | MegaBLAST | Synamatix |
|---|---|---|---|---|
| % of reads with transcript match | 64.7 | 82.4 | 66.5 | 68.5 |
| Transcript CPU Time (hr) | 2.0 | 15.5 | 0.5 | 0.9 |

TABLE 3-continued

Comparison of alignment methods for mapping 621,341 454 reads from SID 1437

| | BLAT | GMAP | MegaBLAST | Synamatix |
|---|---|---|---|---|
| % of reads with genome match | 88.0 | 97.8 | 87.6 | 96.5 |
| Genome CPU Time (hr) | 52.3 | 14.0 | 171.8 | 3.2 |

MegaBLAST v.2.2.15, BLAT v.32x1, GMAP v.2006-04-21 were used to align 454 reads with human RefSeq transcript dB release 16 and human genome release 16, and Synasearch v1.3.1 with RefSeq release 19 and human genome release 36.1. GMAP, BLAT and MegaBLAST alignments were performed on a 62-Dual-core Processor Dell 1855 Blade Cluster with 124 GB RAM and 2.4 TB disk. Synamatix alignments were performed on a dual Intel Itanium 1.5 GHz CPU with 64 GB RAM. Similar figures were obtained with SID 1438 and SID 1439.

Figure 9:
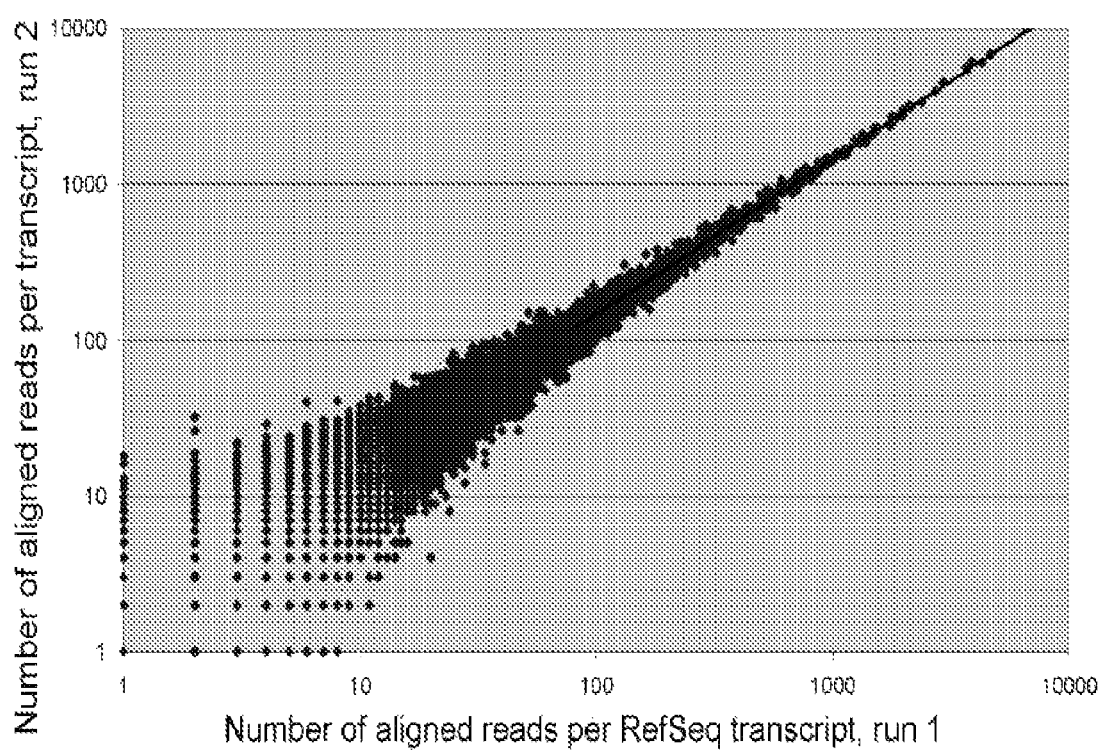
FIG. 9 is a graph showing run-to-run variation in RefSeq transcript read counts.

On the basis of MegaBLAST and GMAP read alignments, it was found that the majority of genes were expressed in lymphoblastoid lines and lung samples. ~55% of genes were detected by >1 aligned read in ~60 MB of lymphoblastoid cDNA MRS data (Table 4). ~75% of genes were detected by >1 aligned read in ~300 MB of lung cDNA MRS data. Very little run-to-run variation was noted in the number of reads aligning to each gene ($r2>0.995$, FIG. 9). FIG. 9 illustrates run-to-run variation in RefSeq transcript read counts. Two runs of 454 sequence were aligned to the RefSeq transcript dB with megaBLAST. In the range examined (up to 1.65 GB per sample type), the number of transcripts with aligned reads and the depth of coverage increased with the quantity of MRS. This was true both of lymphoblastoid cell lines and lung specimens. These data indicate that 3 GB of MRS per sample provide 8x coverage of ~40% of human transcripts (sufficient to unambiguously identify heterozygous nsV, see below) and ~50% of transcripts with 4x coverage (sufficient to unambiguously identify heterozygous nsV).

TABLE 4

RefSeq transcript alignment statistics for 454 sequences from lymphoblastoid cell line RNAs

| Case/Method | 1437 MegaBLAST | 1437 GMAP | 1438 MegaBLAST | 1438 GMAP | 1439 MegaBLAST | 1439 GMAP |
|---|---|---|---|---|---|---|
| Number of reads | 621341 | 621341 | 536463 | 536463 | 586232 | 586232 |
| % reads aligned to a RefSeq transcript | 72 | 64 | 79 | 61 | 64 | 64 |
| % RefSeq transcripts with ≧1 aligned read | 58 | 53 | 57 | 51 | 57 | 52 |
| Number of indels | 704662 | 211882 | 556910 | 177702 | 604920 | 170407 |
| Number of SNPs | 281915 | 204730 | 275277 | 172183 | 253182 | 190491 |
| Indel per kb | 10.8 | 3.3 | 9.9 | 3.2 | 10.0 | 2.8 |
| SNP per kb | 4.3 | 3.1 | 4.9 | 3.1 | 4.2 | 3.2 |

A moderate 3' bias was observed in the distribution of read coverage across transcripts, as anticipated with oligo-dT priming. The bias was not, however, sufficiently pronounced to preclude analysis of 5' regions.

TABLE 5

Schizophrenia Candidate Genes
(from www.polygenicpathways.co.uk)

ACE, ADH1B, APOE, ARVCF, ADRA1A, ATN1, AGA, ATXN1, AHI1, AKT1, ALDH3B1, ALK, APC, B3GAT1, BDNF, BRD1, BZRP, CCKAR, CHGB, CHL1, CHN2, CHRNA7, CLDN5, CNP, CNR1, CNTF, COMT CPLX2, CTLA4, DAO, DAOA, DISC1, DLG2, DPYSL2, DRD2, DRD3, DRD4, DRD5, DTNBP1, EGF, ELSPBP1, ENTH, ERBB4, FEZ1, FOXP2, FZD3, GABBR1, GABRB2, GAD1, GALNT7, GCLM, GFRA1, GNAS, GNPAT, GPR78, GRIA1, GRIA4, GRID1, GRIK3, GRIK4, GRIN1, GRIN2A, GRIN2B, GRIN2D, GRM3, GRM4, GRM5, GRM8, GSTM1, HLA-B, HLA-DRB1, HMBS, HOMER1, HP, HRH2, HTR2A, HTR5A, HTR6, HTR7, IL10, IL1B, IL1RN, IL2, IL4, IMPA2, JARID2, KCNN3, KIF2, KLHL1AS, KPNA3, LGI1, LTA, MAG, MAOA, MAP6, MCHR1, MED12, MLC1, MOG, MPZL1, MTHFR, NAALAD2, NDUFV2, NOS1, NOS1AP, NOTCH4, NPAS3, NPTN, NPY, NQO2, NRG1, NRG3, NTF3, NTNG1, NTNG2, NUMBL, OLIG2, OPRS1, PAH, PAX6, PCM1, PCQAP, PDE4B, PDLIM5, PHOX2B, PICK1, PIK3C3, PIP5K2A, PLA2G4A, PLA2G4B, PLA2G4C, PLP1, PLXNA2, PNOC, PPP3CC, PRODH, PTGS2, RANBP5, RGS4, RHD, RTN4, RTN4R, S100B, SLC15A1, SLC18A1, SLC1A2, SLC6A3, SLC6A4, SNAP29, SOD2, SRR, ST8SIA2, STX1A, SULT4A1, SYN2, SYN3, SYNGR1, TAAR6, TH, TNF, TNXB, TP53, TPH1, TPP2, TUBA8, TYR, UFD1L, UHMK1, XBP1, YWHAH, ZDHHC8, ZNF74

The expression of schizophrenia candidate genes in lymphoblastoid cells was a concern. 172 schizophrenia candidate genes were identified by literature searching (Table 5). 66-68 candidate genes (40%) had >3 reads aligned by GMAP in the three lymphoblastoid lines. Scaling from 50 MB to 3 GB MRS per sample, this read count is equivalent to 8× coverage. Thus, ~40% of schizophrenia candidate genes are evaluated for nSV by lymphoblastoid transcriptome MRS.

The number of SNPs and indels for reads aligned with MegaBLAST and GMAP was enumerated for each sample (Table 4). One effect of the incompleteness of the RefSeq transcript database was that some MegaBLAST best matches that met criteria for reporting were misalignments. This was not observed with GMAP. Read misalignment generated false positive SNP and indel calls. Other causes of SNP and indel calls were true nucleotide variants, RefSeq database errors and 454 basecalling errors. 454 data has a higher basecall error rate than conventional Sanger resequencing, particularly indel errors adjacent to homopolymer tracts. The unfiltered indel rate per kb with MegaBLAST read alignment was 9.9-10.8 per kb, and for GMAP was 2.8-3.3 per kb. The SNP rate per kb with MegaBLAST was 4.2-4.9 per kb, and for GMAP was 3.1-3.2 per kb. In contrast, the true SNP rate per kb in the human genome is ~0.8 per kb and indel rate is approximately 10-fold less than the SNP rate. These data indicated that use of additional filter sets would be necessary to identify high-likelihood, true-positive SNPs and indels in MRS data.

To circumvent the identification of false-positive nucleotide variants, a rule set was developed for SNP and indel identification in 454 reads (Table 6). These rules represent the threshold values of these elements. These filters had been previously validated on a set of ~2.5 million 454 reads and 2,465 previously described human SNPs present in 1,415 genes in a human lung RNA sample and it was found that 96% of known SNPs were detected. Application of these filters via the disclosed methods reduced the number of genes with nsV by 60-fold.

TABLE 6

Rules for identification of high-likelihood, true-positive SNPs and indels in 454 transcriptome MRS:

Variant present in ≧4 reads
Variant present in ≧30% of reads
High quality score at variant base
Present in 5'→3' and 3'→5' reads An example of the utility of application of these bioinformatic filters is shown in FIG. 7. SNPs were 3-times more common than indels (Table 7). The relative frequency of genes with CD sSNP and nsSNP was similar. The frequency of genes with SNPs in untranslated regions (UTRs) was 2-fold greater than in CDs, in agreement with the lung MRS data8. nsSNPs causing premature stop codons were rare. CD SNPs were 7-fold more common than indels. The ratio of the number of reads with wild-type and variant allele nucleotides appeared able to infer homozygosity and heterozygosity, as previously validated. In the pedigree, inheritance patterns of alleles inferred from read-ratios agreed well with identity by descent and inheritance rules.

TABLE 7

Variants identified by GMAP alignment of SID 1437 cDNA 454 reads to the RefSeq transcript dB without and with bioinformatics filters

| Genes with aligned reads | Unfiltered | Filtered |
| --- | --- | --- |
| With ≧1 SNP | 11,459 (40%) | 932 (3%) |
| With ≧1 coding domain SNP | 7595 (26%) | 356 (1%) |
| With ≧1 coding domain, synonymous SNP | 4933 (17%) | 238 |
| With ≧1 non-synonymous SNP (nsSNP) | 6891 (24%) | 199 |
| With a SNP causing a premature stop codon | 1660 (6%) | 4 |
| With ≧1 indel | 11,313 (39%) | 313 (1%) |
| With ≧1 coding domain indel | 8,372 (29%) | 54 |

Further, distributed characterization of nsV (nsSNPs and CD indels) was undertaken with the disclosed methods, in order to identify a subset of candidate genes likely to be associated with medically relevant functional changes in schizophrenia. A second rule set was developed to identify high-likelihood, medically relevant nsV (Table 8). These rules represent a second set of threshold values for these elements. Particularly important at this stage were inspection of the quality of read alignment and BLAST comparison of the read to a second database. ~10% of nsSNPs were RefSeq transcript database errors and the reads matched perfectly to the NCBI human genome sequence or, upon translation, to protein sequence databases. BLOSUM scores were calculated, but were not used to triage candidate genes, since nsSNPs in complex disorders nsSNPs are strongly biased toward less deleterious substitutions. Congruence with altered gene or protein expression in brains of patients with schizophrenia was ascertained by link-out to the Stanley Medical Research Institute database. Congruence with altered gene expression is important in view of recent studies showing that SNPs are responsible for >84% of genetic variation in gene expression. Functional plausibility of the candidate gene was ascertained by link-outs to OMIM, ENTREZ gene and PubMed. Confluence of candidate genes into networks or pathways was considered highly significant, given the likelihood of pronounced genetic heterogeneity. Pathway analysis was performed both by evaluation of standard pathway databases, such as KEGG, and also by custom database creation and visualization of interactions among these genes using Ariadne Pathways software (Ariadne Genomics, Rockville, Md.).

TABLE 8

Rules for identification of high-likelihood, medically relevant nsV in transcriptome MRS studies >90% read alignment to reference sequence
Exclude reference sequence error by alignment to $2^{nd}$ reference dB (e.g. if initial alignment to RefSeq transcript, confirm by alignment to NCBI human genome)
BLOSUM62 score
nsV congruence in parent-child trio, ASP or pedigree
Confluence of nsV into network or pathway
Functional plausibility (ENTREZ, OMIM)
Chromosomal location with QTL
Congruence with gene or protein expression data (for example, Stanley dB, and the like)

Of the 172 schizophrenia candidate genes (Table 5), 3 (HLA-B, HLA-DRB1 and KIF2) exhibited a nsSNP in the proband, and 2 (LTA, UHMK1) had a nsSNP in one of the other cases. KIF2 contained a novel nsSNP (a821g) at all aligned reads in SID1437 and SID1439. No reads aligned at this location in SID1438. KIF2 is important in the transport of membranous organelles and protein complexes on microtubules and is involved in BDNF-mediated neurite extension. A prior study of transmission disequilibrium in a cohort of affected family samples identified a common two-SNP haplotype (rs2289883/rs464058, G/A) that showed a significant association with schizophrenia, as did a common four-SNP haplotype ($P<0.008$).

TABLE 9 nsV identified in three lymphoblastoid lines by GMAP alignment to RefSeq transcript following application of bioinformatics filters

| Genes with aligned reads and filtering | SID1437 | SID1438 | SID1439 | All |
|---|---|---|---|---|
| ≧1 nsSNP | 199 | 202 | 252 | 74 |
| SNP-induced premature stop codon | 4 | 4 | 6 | 0 |
| ≧1 coding domain indel | 54 | 78 | 123 | 5 |

Seventy-nine genes had a nsV in all 3 individuals (Table 9). Of these, four were RefSeq transcript database errors. Ten were in highly polymorphic HLA genes, including two in schizophrenia candidate genes HLA-B and HLA-DRB1. Thirty-one occurred in putative genes that have been identified informatically from the human genome sequence. nsV within such genes were found to be unreliable due to: i) uneven coverage (likely misannotation of splice variants), ii) an overabundance of putative SNPs, and/or iii) premature truncation of alignments. Of the remaining 36 genes, ADRBK1, GSTP1, MTDH, PARP1, PLCG2, PLEK, SLC25A6, SLC38A1 and SYNCRIP were particularly interesting since they were related to schizophrenia candidate genes (Table 10).

TABLE 10

Genes related to candidates with nsV in SID 1437

| Function | Candidate Gene | Related Gene With nsV in SID 1437 |
|---|---|---|
| Glutamate receptor agonist availability | NAALAD2 | DPP7 |
| | SLC15A1 | SKC25A6 |
| | PRODH | P4HA1 |
| | SLC1A2 | SLC38A1 |
| | DTNBP1 | VAPA |
| | ENTH | FLNA |
| Synaptic vesicle exocytosis | SNAP29 | ACTN4 |
| | SYN2 | ANXA11, ANXA2 |
| | SYN3 | MTDH |
| | STX1A | SYNCRIP |
| | SYNGR1 | SNX3 |
| Plasticity | PLXNA2 | PLEK |
| Cytokine-related | PIP5K2A | PLCG2 |
| Glutathione | GSTM1, GCLM | GPX1, GSTP1 |
| Postsynaptic density | ADRA1A | ADRBK1 |
| | MED12 | PAPOLA, PAP1, PCB1 |
| | MAP6 | MARK3 |

Of 244 genes with an nsV in the proband (Table 9), seven were RefSeq transcript database errors, 71 were in putative genes and twelve were in HLA genes. Twenty-one genes had a nsV in the proband that were either close relatives of schizophrenia candidate genes or in the same pathway (Table 10). Notable were GPX1 and GSTP1, both of which contained known nsSNPs (rs1050450 and rs1695 and rs179981, respectively). GPX1 and GSTP1 are important in glutathione metabolism. Glutathione is the main non-protein antioxidant and plays a critical role in protecting neurons from damage by reactive oxygen species generated by dopamine metabolism. A large literature exists regarding glutathione deficiency in prefrontal cortex in schizophrenia and several groups have sought associations between glutathione metabolism genes or polymorphisms with schizophrenia and tardive dyskinesia. Mendelian deficiency in glutathione metabolism genes results in mental deficiency and psychosis. An interesting follow-up study would be to seek association between the endophenotype of prefrontal glutathione level (measured by NMR spectroscopy) and GPX1 and GSTP1 genotypes.

Also notable were numerous genes involved in synaptic vesicle exocytosis (ACTN4, ANXA11, ANXA2, MTDH, SYNCRIP, SNX3).

Interestingly, two nsV identified by GMAP were associated with novel splice isoforms (KHSRP, FIG. 10 and FIG. 11, and SYNCRIP, FIG. 12). In the case of KHSRP, the nsSNP was an artifact of GMAP-based alignment extension through a hexanucleotide hairpin that was present at the 3' terminus of both exon 19 and intron 19. A novel KHSRP splice isoform was identified that retains intron 19 sequences. The novel SYNCRIP splice isoform omits an exon present in the established transcript.

Figure 13:
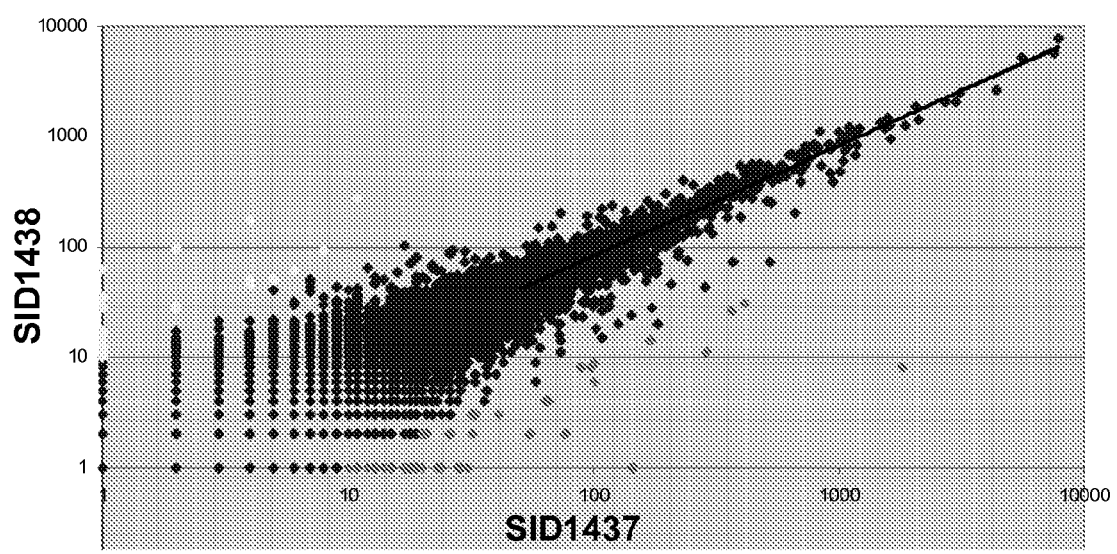
FIG. 13 is a graph showing the results of pairwise comparisons of the copy numbers of individual transcripts in lymphoblast cell lines from related individuals showed significant correlation.

Since next generation sequencing technologies generate clonal sequences from individual mRNA molecules, enumeration of aligned reads permits estimation of the copy number of transcripts, splice variants and alleles. As noted above, the aligned read counts for individual transcripts in a sample showed little run-to-run variation (FIG. 9). Read count was affected by the length of the transcript, the fidelity of alignment, and the repetitiveness of transcript sub-sequences. In particular, some transcripts with repetitive sequences within the 3' UTR exhibited significant local increases in read counts at those regions, as has been described for pyknons and short tandem repeats. Thus, comparisons of read count-based abundance of different transcripts within a sample were not always accurate. However, comparisons of abundance of a transcript between samples that were based upon read counts were accurate, as previously validated. Pairwise comparisons of the copy numbers of individual transcripts in lymphoblast cell lines from related individuals showed significant correlation (FIG. 13, $r^2>0.93$) and allowed identification of transcripts exhibiting large differences in read count between individuals.

Figure 10A:
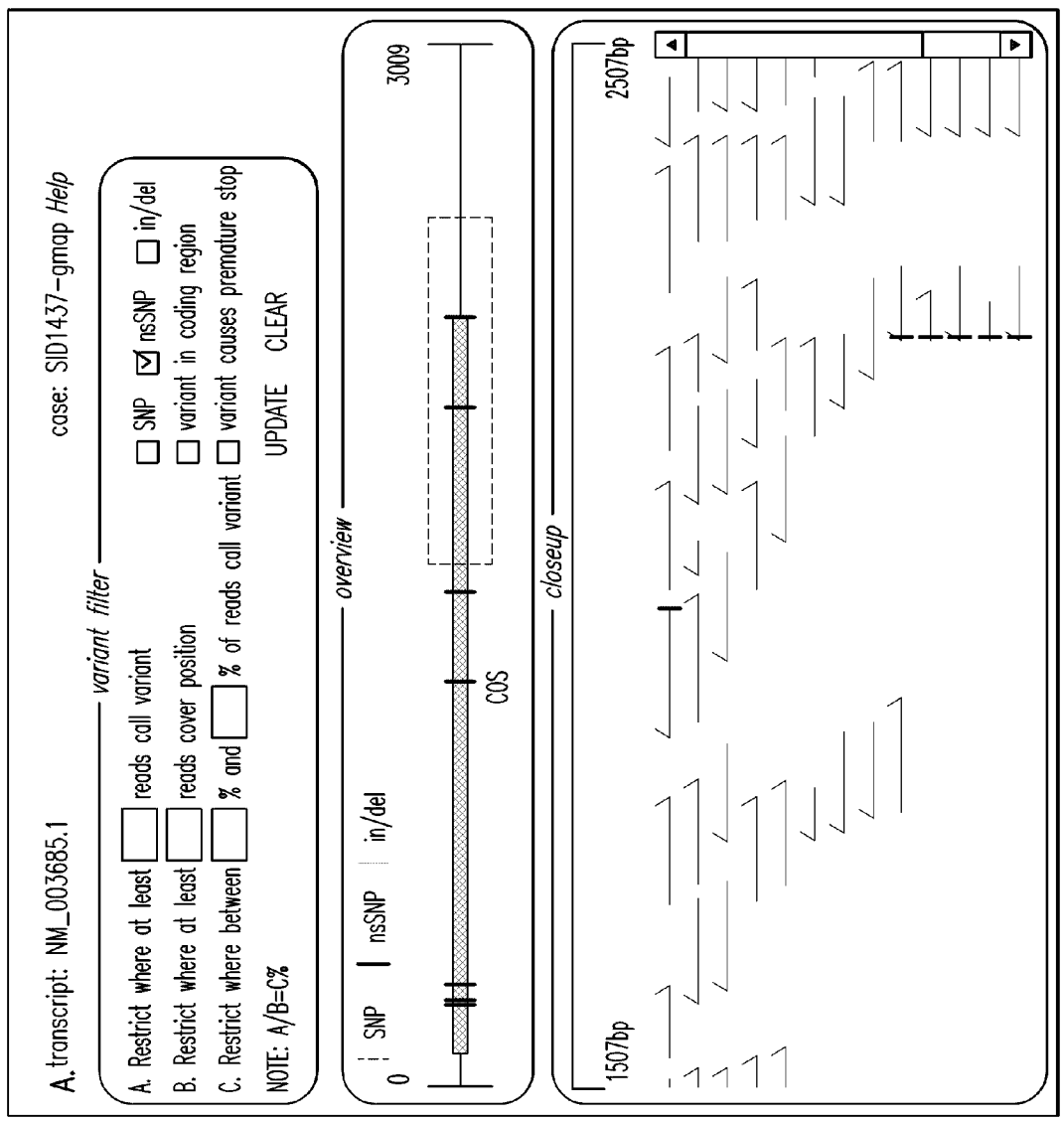

FIG. 10A-C and FIG. 11 illustrate an example of a novel splice isoform identified with GMAP by an apparent SNP at the penultimate base of an alignment. FIG. 10A illustrates GMAP based alignment of SID1437 reads to nucleotides 1507-2507 of KHSRP transcript NM_003685.1, showing a nsSNP in five of twelve reads (red line, a2216c, inducing a Q to C non-conservative substitution, BLOSUM score −1). FIG. 10B illustrates the FASTA-format of the GMAP alignment of one of the five cDNA reads containing a nsSNP (D93AXQM01ARQC5) to KHSRP transcript NM_003685.1. Note that only the 3' 50 nt of the read aligned to this transcript. The nsSNP is indicated in yellow, the stop codon in red, and a stable hexanucleotide hairpin in green. Score=0bits (50), Identities=50/50 (98%), Strand=+/+. FIG. 10C illustrates alignment of the entire read D93AXQM01ARQC5 to KHSRP intron 19 and exon 20. Chr19 nucleotides refer to contig reflNW_927173.1|HsCraAADB02_624. The nucleotide that corresponded to a nsSNP when aligned to NM_003685.1 shows identity when aligned against Chr19 (yellow). The stop codon is indicated in red, a stable hexanucleotide hairpin in green and exon 20 in grey. Score=204 bits (110), Expect=2e-50, Identities=100%, Gaps=0%, Strand=+/−.

FIG. 11 illustrates the genomic sequence of KHSRP exon 19 (purple), exon 20 (grey) and the 3' end of intron 19 (blue) which is present in 5 cDNA reads (including D93AXQM01ARQC5). Apparent nsSNP when aligned to NM_003685.1 shows identity when aligned against Chr19 (indicated in yellow). The stop codon is indicated in red and a stable hexanucleotide hairpin in green. Interestingly, the hairpin sequence flanks the splice donor site of exon 19 and splice acceptor site of intron 19, indicating a possible mechanism whereby KHSRP may be alternatively spliced to retain intron 19 sequences.

FIG. 12 illustrates a GMAP alignment of read D9VJ59F02JQMRR (nt 1-109, top) from SID 1438, to SYN-CRIP (NM_006372.3, bottom) showing a nsSNP at nt 30 (yellow, a1384g) and a novel splice isoform that omits an 105-bp exon and maintains frame. Consensus splice donor and acceptor nucleotides are in red. Four reads demonstrated the nsSNP. Score=0 bits (119), Identities=109/119 (98%).

In summary, ~150 MB of shotgun, clonal, cDNA MRS of lymphoblastoid lines from a pedigree with mental illness was performed, using approaches developed for a prior ~2 GB MRS study in cancer. Automated data pipelining and distributed, facilitated analysis was accomplished using web-based cyberinfrastructure. A two-tiered analysis schema identified twenty-one schizophrenia candidate genes that showed reasonable accord with current understanding of the molecular pathogenesis of schizophrenia (Table 10).

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A computer-implemented method of identifying elements associated with a trait, the method comprising selecting a set of discovery samples, wherein the set of discovery samples consist of samples from a single individual, samples from a single pedigree, samples from a subset of a single cohort, or samples from a single cohort;

identifying, by the computer, variant genetic elements in the discovery samples;

filtering, by the computer, the variant genetic elements to select candidate variant genetic elements, wherein the variant genetic elements are filtered by selecting variant genetic elements that are present in a threshold number of sequence reads, are present in a threshold percentage of sequence reads, are represented by a threshold read quality score at variant base(s), are present in sequence reads from in a threshold number of strands, are aligned at a threshold level to a reference sequence, are aligned at a threshold level to a second reference sequence, are variants that do not have biasing features bases within a threshold number of nucleotides of the variant or a combination;

prioritizing, by the computer, the candidate variant genetic elements to select relevant variant genetic elements; and identifying, by the computer, an association of a relevant element with a relevant component phenotype of the trait, wherein the relevant element is selected from the relevant variant genetic elements and wherein the relevant element is an element having a threshold value of importance of the element to homeostatis relevant to the trait, intensity of the perturbation of the element, duration of the effect of the element, or a combination, wherein the relevant component phenotype is a component phenotype having a threshold value of severity, age of onset, specificity to the trait, or a combination, and wherein the association of the relevant element with the relevant component phenotype identifies the relevant element as an element associated with the trait.

2. The method of claim 1, wherein the association of the relevant element with the relevant component phenotype is identified by identifying the association of the relevant element with a network or pathway associated with the relevant component phenotype.

3. The method of claim 2, wherein the network or pathway is associated with the relevant component phenotype when the relevant component phenotype occurs or is affected when the network or pathway is altered.

4. The method of claim 1, wherein the association of the relevant element with the relevant component phenotype is identified by a threshold value of the coincidence of the relevant element and the relevant component phenotype within a set of discovery samples.

5. The method of claim 4, wherein the set of discovery samples consist of samples from a single individual, samples from a single pedigree, samples from a subset of a single cohort, samples from a single cohort, samples from multiple individuals, samples from multiple unrelated individuals, samples from multiple affected sib-pairs, samples from multiple pedigrees, or a combination.

6. The method of claim 5, wherein the set of discovery samples include both affected samples and unaffected samples, wherein affected samples are samples associated with the relevant component phenotype, wherein unaffected samples are samples not associated with the relevant component phenotype.

7. The method of claim 1, wherein the trait is a disease, a phenotype, a quantitative or qualitative trait, a disease outcome, or a disease susceptibility.

8. The method of claim 1, wherein the relevant element further is an element associated with one or more genetic elements associated with the trait.

9. The method of claim 8, wherein the one or more genetic elements are derived from DNA sequence data, genetic linkage data, gene expression data, antisense RNA data, microRNA data, proteomic data, metabolomic data or a combination.

10. The method of claim 1, wherein the relevant component phenotype further is a component phenotype associated with a network or pathway of interest.

11. The method of claim 10, wherein the relevant component phenotype is a component phenotype specific to the network or pathway of interest.

12. The method of claim 1, wherein the relevant element is a relevant genetic element.

13. The method of claim 1, wherein the threshold value of importance of the element to homeostatis relevant to the trait is derived from the phenotype of knock-out, transgenesis, silencing or overexpression of the element in an animal model or cell line; the phenotype of a genetic lesion in the element in a human or model inherited disorder; the phenotype of knock-out, transgenesis, silencing or overexpression of an element related to the element in an animal model or cell line;
the phenotype of a genetic lesion in an element related to the element in a human or model inherited disorder; knowledge of the function of the element in a related species, or a combination.

14. The method of claim 13, wherein the element related to the element is a gene family member or an element with sequence similarity to the element.

15. The method of claim 1, wherein the threshold value of intensity of the perturbation of the element is derived from the type of element, the amount or level of the element, or a combination.

16. The method of claim 15, wherein the relevant element is a relevant genetic element, wherein the type of element is a type of genetic variant, wherein the type of genetic element is a regulatory variant, a non-regulatory variant, a non-synonymous variant, a synonymous variant, a frameshift variant, a variant with a severity score at, above, or below a threshold value, a genetic rearrangement, a copy number variant, a gene expression difference, an alternative splice isoform, or a combination.

17. The method of claim 15, wherein the relevant element is a relevant genetic element, wherein the amount or level of the element is the number of copies of the relevant genetic element, the magnitude of expression of the genetic element, or a combination.

18. The method of claim 1, wherein the element is an environmental condition, wherein the threshold value of duration of the effect of the element is derived from the duration of an environmental condition or the duration of exposure to an environmental condition.

19. The method of claim 1, wherein the element is a genetic element, wherein the threshold value of duration of the effect of the element is derived from the duration of expression of the genetic element, the expressivity of the genetic element, or a combination.

20. The method of claim 1, wherein the threshold value of severity of the component phenotype is derived from the frequency of the component phenotype, the intensity of the component phenotype, the amount of a feature of the component phenotype, or a combination.

21. The method of claim 1, wherein the threshold value of specificity to the trait of the component phenotype is derived from the frequency with which the component phenotype is present in other traits, the frequency with which the component phenotype is present in the trait, or a combination.

22. The method of claim 21, wherein the component phenotype is not present in other traits.

23. The method of claim 21, wherein the component phenotype is always present in the trait.

24. The method of claim 21, wherein the component phenotype is not present in other traits and is always present in the trait.

25. The method of claim 1 further comprising selecting an element as the relevant element by assessing the value of importance of the element to homeostatis relevant to the trait, intensity of the perturbation of the element, duration of the effect of the element, or a combination and comparing the value to the threshold value.

26. The method of claim 1 further comprising selecting a component phenotype as the relevant component phenotype by assessing the value of clinical features of the phenotype, and comparing the value to the threshold value.

27. The method of claim 26, wherein the clinical features of the phenotype comprise the value of severity, age of onset, duration, specificity to the phenotype, response to a treatment or a combination.

28. The method of claim 1 further comprising selecting a component phenotype as the relevant component phenotype by assessing the value of laboratory features of the phenotype, and comparing the value to the threshold value.

29. The method of claim 1, wherein the variant genetic elements are identified by sequencing nucleic acids from the discovery samples and comparing the sequences to one or more reference sequence databases.

30. The method of claim 29, wherein the comparison involves, but is not limited to, BLAST alignments, megaBLAST alignments, GMAP alignments, BLAT alignments or a combination.

31. The method of claim 29, wherein the reference sequence database is, but not limited to, the RefSeq genome database, the transcriptome database, the GENBANK database, or a combination.

32. The method of claim 1, wherein the variant genetic elements identified in the discovery samples are part of a catalog of variant genetic elements identified in a plurality of sets of discovery samples.

33. The method of claim 1, wherein the candidate variant genetic elements are prioritized according to the presence in the candidate variant genetic element of a non-synonymous variant in a coding region, the presence of the candidate variant genetic element in a plurality of samples, the presence of the candidate variant genetic element at a chromosomal location having a quantitative trait locus associated with the trait, the severity of the putative functional consequence that the candidate variant genetic element represents, the association of the candidate variant genetic element with a network or pathway in a plurality of samples, the association of the candidate variant genetic element with a network or pathway with which one or more other candidate variant genetic elements are associated, the plausibility or presence of a functional relationship between the candidate variant genetic element and the relevant component phenotype, or a combination.

34. The method of claim 1, wherein the association of a relevant element with a relevant component phenotype of the trait is performed for a plurality of relevant elements, a plurality of relevant component phenotypes of the trait, or a plurality of relevant elements and a plurality of relevant component phenotypes of the trait.

35. The method of claim 1, further comprising validating the association of the relevant element with the relevant component phenotype.

36. The method of claim 35, wherein association of the relevant element with the relevant component phenotype is validated by assessing the association of the relevant element with the relevant component phenotype in one or more sets of validation samples, wherein the set of validation samples is different than the samples from which the relevant element was selected.

37. The method of claim 36, wherein the set of validation samples consist of samples from a single individual, samples from a single pedigree, samples from a subset of a single cohort, samples from a single cohort, samples from multiple individuals, samples from multiple unrelated individuals, samples from multiple affected sib-pairs, samples from multiple pedigrees, or a combination.

* * * * *

SEQUENCE LISTING

<160> NUMBER OF SEQ ID NOS: 9

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 1
ccgcaggctc aatgaatcga atgaatgtga acttcttcat ctgtgaaaaa     50

<210> SEQ ID NO 2
<211> LENGTH: 50
<212> TYPE: DNA
<213> ORGANISM: Artificial Sequence
<220> FEATURE:

-continued

<223> OTHER INFORMATION: Description of Artificial Sequence: Note =
     Synthetic Construct

<400> SEQUENCE: 2
cagcaggctc aatgaatcga atgaatgtga acttcttcat ctgtgaaaaa                50

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Note =
     Synthetic Construct

<400> SEQUENCE: 3
ccgcccccta gtctcccacc cttccctccc cgtagtgacc aattcctatc tcttccctct    60

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Note =
     Synthetic Construct

<400> SEQUENCE: 4
ccgcccccta gtctcccacc cttccctccc cgtagtgacc aattcctatc tcttccctct    60

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Note =
     Synthetic Construct

<400> SEQUENCE: 5
ccgcaggctc aatgaatcga atgaatgtga acttcttcat ctgtgaaaaa                50

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Note =
     Synthetic Construct

<400> SEQUENCE: 6
ccgcaggctc aatgaatcga atgaatgtga acttcttcat ctgtgaaaaa                50

<210> SEQ ID NO 7
<211> LENGTH: 1079
<212> TYPE: DNA
<213> ORGANISM: Artificial Sequence
<220> FEATURE:
<223> OTHER INFORMATION: Description of Artificial Sequence: Note =
     Synthetic Construct

<400> SEQUENCE: 7
cgccgcccac gcagcaggga cagcagcagg caagtgggaa ttgccaccct cctcctcctc     60
ctttctcctt ccaaccccccg gccaccgtcc atcctgcctt agtgggtagc gccgaaaacc   120
ccttcccctg cggggtgtgc ccttgatgcc tgcagcgggg gccgtgtggc cggaggtctc   180
cgggagtccc cacgcaccgc cagggaagca ttcgctgggt ccagaggtta aacgaagagg   240
cctccctgcg ccggctgctt gttcctgtgt gccgctgtcg tgatgctggg gagcgctgag   300

-continued

```
actcgcaggc gggacttctg aactgctggg gagtcggggg gcaggcagac agcgcggacg    360
gtgggcaccg gcccggccgc caccactcgc tcacaatctg gccacttggg aagaaaacgt    420
ctattttttc cccttctctg catcactttt ttggtttttg ttcttttat tcttttattt    480 tttaaaccca tgatctttt tcctgtgtcc aagtgactgt gttgcaggcg gcccggctct    540
ggcagggact ggtggggacg cggggagcgg cccaggcccc tgcccgccg ggctcagcct    600 cccatgcgct cgcgcttgcc tgtgtcccgg gcttgtctgt gaagtgggcg tgaagatcgt    660
tgccaccttc caacctacct cacaggggtg ttgtggggac accatgatct ctggattgtt    720
catgtcgttg tgctgcgccg ggagccaccg ccctccggag acagggcagc tccctacga    780 ccctagcgcc tccgccctcc gcggccctc tcctctcttc ctgctctgtc cctccttctc    840
catcagggag cagcgtgact tcagcgagtc ccgcgagcac ctggctagac agttaacaag    900
cacgtccttc cagcctgagc cagcgcaggt tgggaggggg cttcctggcc cccccacgg    960 tgttccagcc cctcctctct tccgcccct agtctcccac ccttccctcc ccgtaggacc    1020
aattcctatc tcttccctct ccgcaggctc aatgaatcga atgaatgtga acttcttca    1079
```

<210> SEQ ID NO 8
<211> LENGTH: 109
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 8

```
ccaccaaccg gatgacaaga aaaaaacaga ggcttttgct ttcttgaata tgaagatcac     60
aaaacagctg cccaggtaaa agtgctgttt gtacgcaacc ttgccaata              109
```

<210> SEQ ID NO 9
<211> LENGTH: 116
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 9

```
ccaccaaccg gatgacaaga aaaaaaacag gagcttttgc tttcttgaat atgaagatca     60
caaaacagct gcccaggcaa aggtaaaagt gctgtttgta cgcaaccttg ccaata        116
```